United States Patent [19]

Dumont

[11] Patent Number: 5,663,174

[45] Date of Patent: Sep. 2, 1997

[54] AROMATIC SULFONAMIDE DERIVATIVES, THEIR USE AS ENZYME INHIBITORS AND PHARMACEUTICAL COMPOSITIONS CONTAINING THEM

[75] Inventor: Raymond Dumont, Gränichen, Switzerland

[73] Assignee: Pharno-Wedropharm GmbH, Germany

[21] Appl. No.: 785,251

[22] Filed: Jan. 17, 1997

Related U.S. Application Data

[63] Continuation of Ser. No. 204,317, filed as PCT/EP91/01678 Sep. 5, 1991, abandoned.

[51] Int. Cl.$^6$ .................. A61K 31/495; A61K 31/18; C07D 403/06; C07C 311/14

[52] U.S. Cl. .................. 514/252; 514/253; 514/255; 514/307; 514/419; 514/423; 514/602; 514/604; 544/363; 544/372; 544/373; 544/391; 546/146; 548/495; 548/537; 564/84; 564/92; 564/94

[58] Field of Search .................. 544/363, 391, 544/372, 373; 546/146; 548/495, 537; 564/84, 92, 94; 514/253, 255, 307, 419, 423, 602, 604, 252

[56] References Cited

U.S. PATENT DOCUMENTS

| | | | |
|---|---|---|---|
| 4,525,589 | 6/1985 | Hidaka et al. | 544/363 |
| 4,537,896 | 8/1985 | Claeson et al. | 514/330 |
| 4,560,755 | 12/1985 | Hidaka et al. | 544/363 |
| 4,678,783 | 7/1987 | Hidaka et al. | 514/218 |
| 5,081,246 | 1/1992 | Hidaka et al. | 544/363 |
| 5,216,150 | 6/1993 | Hidaka et al. | 540/597 |
| 5,244,895 | 9/1993 | Hidaka et al. | 544/363 |

FOREIGN PATENT DOCUMENTS

| | | |
|---|---|---|
| 0061673 | 10/1982 | European Pat. Off. . |
| 0138720 | 4/1985 | European Pat. Off. . |
| 0187371 | 7/1985 | European Pat. Off. . |
| 0287696 | 10/1988 | European Pat. Off. . |
| 0333557 | 9/1989 | European Pat. Off. . |
| 2218787 | 4/1972 | Germany . |
| 09787 | 9/1990 | WIPO . |

OTHER PUBLICATIONS

Kyowa Hakko Kogyo Co., *Chemical Abstracts*, vol. 94 No. 156735 (1981) (Abstract for JP 80 81,857 Jun. 20, 1980).
El-Naggar et al, *Chemical Abstracts*, vol. 94, No. 84465 (1981).
Teslenko et al, *Chemical Abstracts*, vol. 60, No. 10779g (1964).
Behrens et a, *Chemical Abstracts*, vol. 114, No. 121774 Abstract for WO 90 09787, Sep. 7, 1990 (1991).
Hidaka et al, *Chemical Abstracts*, vol. 107, No. 154355 (1987) Abstract for JP 62 87,581, Apr. 22, 1987.
Chijiwa et al., *J. Biol., Chem* 264, pp. 4924–4927 (1989).
W. H. Schuller, et al., "The Papain-catalyzed Synthesis of Acyl-D and L-Phenylalanylphenyl-hydrazides from a Series of Enantiomorphic Pairs of Acylated Phenylalanines," J.A.C.S., vol. 73,m (Apr., 1951) pp. 1644–1646.
L. Goldman, et al., "Anticonvulsants. Benzyl 4-Carbamyl-1-piperazine-carboxylate and Related Compounds," *J. Org. Chem.*, vol. 18, (1953) pp. 815–821.
T. F. Buckley, et al., "α-Amino Acids as Chiral Educts for Asymmetric Products. Amino Acylation with N-Acylamino Acids," J.A.C.S., vol. 103, No. 20, (1981) pp. 6157–6163.
R. C. Hart, et al., "Synthesis and Characterization of Calmodulin Antagonistic Drugs," *Methods in Enzymology*, vol. 102, (1983) pp. 195–204.
C. G. Knudsen, et al., "α-Amino Acids as Chiral Educts for Asymmetrical Products. Aminoacylation of Metallo Alkyls and Alkenyls," *J. Org. Chem.*, vol. 48, (1983) pp. 2260–2266.
P. J. Maurer, (H. Rapoport) et al., "α-Amino Acids as Chiral Educts for Asymmetric Products. A General Synthesis of D-α-Amino Acids from L-Serine," J.A.C.S.,vol. 106, (1984) pp. 1095–1098.
G. Skopp, et al., "Synthese des Calmodulinantagonisten N-(6-Aminohexyl)-5-chlor-1-naphthalinsulfonamide (W-7)," *Arch. Pharm.*, vol. 317, No. 84, (1984) pp. 649–650.
G. J. Atwell, et al., "Monoprotection of α,ω-Alkanediamines with the N-Benzyloxycarbonyl Group," *Synthesis*, (Dec. 1984) pp. 1032–1033.
F. Alonso, et al., "A Cytosolic Phospholipase in Human Neutrophils that Hydrolyzes Arachidonoyl-containing Phosphatidylcholine", *Biochim. Biophys. Acta*, vol. 878, (1986) pp. 273–280.
W. C. Ripka, et al., "Molecular Modeling in the Design of Phospholipase A2 Inhibitors," *J. Cell. Biochem.*, vol. 40, (1989) pp. 279–286.
Masatoshi et al. *Chemical Abstracts*, 105:56886x, 1986.
*Patent Abstracts of Japan*, vol. 11, No. 297, p. 93 C 448, Appln. No. 60–226405, 1987.
Juszozak et al. *Chemical Astracts*, 110:93380b, 1989.
Chijawa et al. *Chemical Abstracts*, 110:227610n, 1989.
Tokumitsu et al. *Chemical Abstracts*, 112:233042m, 1990.
Hiromichi, *Chemical Abstracts*, 114:234866m, 1991.

*Primary Examiner*—Emily Bernhardt
*Attorney, Agent, or Firm*—David L. Mossman

[57] ABSTRACT

Aromatic sulfonamide derivatives, particularly benzenesulfonamide, 4-fluorobenzenesulfonamide, 5-chloro-1-naphthalenesulfonamide and 5-isoquinolinesulfonamide derivatives are provided that inhibit $Ca^{2+}$-dependent enzymes and proteins such as Phospholipase $A_2$, protein kinases such as Protein Kinase C, and inhibit membrane fusion, thereby being a valuable drug for the treatment of inflammation, arthritis, infarction, nephritis and many other types of tissue injury.

31 Claims, No Drawings

AROMATIC SULFONAMIDE DERIVATIVES, THEIR USE AS ENZYME INHIBITORS AND PHARMACEUTICAL COMPOSITIONS CONTAINING THEM

This is a continuation of application Ser. No. 08/204,317, filed as PCT/EP91/01678 on Sep. 5, 1991, now abandoned.

This invention relates to aromatic sulfonamide derivatives, especially to benzenesulfonamide-, 4-fluorobenzenesulfonamide-, 5-chloro-1-naphthalenesulfonamide- and 5-isoquinolinesulfonamide derivatives.

This invention particularly relates to aromatic sulfonamide derivatives that inhibit $Ca^{2+}$-dependent enzymes and proteins such as Phospholipase $A_2$, thereby being a valuable drug for the treatment of inflammation, and provides a process for the preparation thereof.

The aromatic sulfonamide derivatives of this invention potentially have promise for inhibiting protein kinases such as Protein Kinase C, and membrane fusion, thereby possibly being drugs for the treatment of arthritis, infarction, nephritis and many other types of tissue injury.

The invention further relates to pharmaceutical compositions containing these derivatives.

BACKGROUND OF THE INVENTION

Literature pertinent to the invention includes the following documents:

L. Goldman & J. H. Williams, *J. Org. Chem.*, Vol. 18, p. 815 (1953).

W. H. Schuller & C. Niemann, *J.A.C.S.*, Vol. 73, p. 1644 (1951).

T. F. Buckley & H. Rapoport, *J.A.C.S.*, Vol. 103, p. 6157 (1981).

C. G. Knudsen & H. Rapoport, *J. Org. Chem.*, Vol. 48, p. 2260 (1983).

H. Rapoport, et al., *J.A.C.S.*, Vol. 106, p. 1095 (1984).

G. J. Atwell & W. A. Denny, *Synthesis*, p. 1032 (1984).

G. Skopp & G. Schwenker, *Arch. Pharm.*, Vol. 317, p. 649 (1984).

R. C. Hart, et al., *Methods in Enzymology*, Vol. 102, p. 195 (1983).

H. Hidaka, European Patent 0187371 (1985).

T. Matsui, et al., *J. Soc. Org. Synth. Chem. Japan*, Vol. 13, p. 320 (1985).

F. Alonso, et al., *Biochim. Biophys. Acta*, Vol. 878, p. 273 (1986).

W. C. Ripka, et al., *J. Cell. Biochem.*, Vol. 40, p. 279 (1989).

SUMMARY OF THE INVENTION

The invention relates to compounds of the general formula:

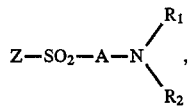

wherein

Z is phenyl, naphthyl, (5)- or (8)-isoquinolyl, possibly substituted by halogen;

A is an amino acid group where the N atom of the amino acid group is bound to $SO_2$ and its carboxyl group to the N atom of formula I $R_1$ is hydrogen, and $R_2$ is phenyl, biphenyl, a $C_2$ to $C_6$-alkylamine or $R_1$ and $R_2$ together form the piperazine ring and its pharmaceutically acceptable non-toxic acid addition salts with inorganic or organic acids.

In another embodiment, the compounds of I have one of the following formulae:

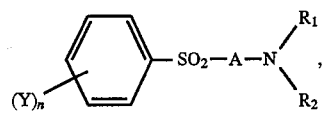

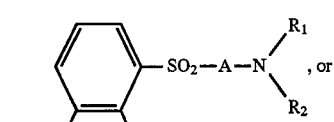

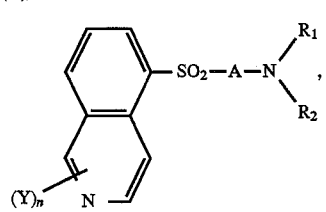

wherein

A, $R_1$ and $R_2$ have the meaning as defined above with respect to formula I,

Y is F, Cl, Br, being the same or different, and n is 0, 1, or 2.

DETAILED DESCRIPTION

The invention is defined in detail in the claims.

A groups in formulae I–IV particularly include L-phenylalanine, L-alanine, L-proline, L-valine, n-tryptophane and L-tyrosine—where the N atom is bound to the $SO_2$ group.

When the $R_1$ group in formulae I–IV is hydrogen, then the $R_2$ group is benzyl, biphenyl or a $C_3$ or $C_6$ alkylene chain. A 6 membered heterocyclic ring (piperazine) may be formed through an ethylene group and adjacent nitrogen atoms.

Exemplary benzenesulfonamide derivatives of the invention include:

(1) N-benzenesulfonyl-L-phenylalanine piperazineamide [referred to as compound 1];

(2) N-benzenesulfonyl-L-alanine piperazineamide [referred to as compound 2];

(3) N-benzenesulfonyl-L-valine piperazineamide [referred to as compound 3];

(4) N-benzenesulfonyl-L-proline piperazineamide [referred to as compound 4];

(5) N-benzenesulfonyl-L-phenylalanine-1,6-diaminohexaneamide [referred to as compound 5];

(6) N-benzenesulfonyl-L-phenylalanine-1,3-diaminopropaneamide [referred to as compound 6];

(7) N-benzenesulfonyl-L-phenylalanine biphenylamide [referred to as compound 7];

(8) N-benzenesulfonyl-L-alanine biphenylamide [referred to as compound 8];

(9) N-benzenesulfonyl-L-valine biphenylamide [referred to as compound 9];

(10) N-benzenesulfonyl-L-proline biphenylamide [referred to as compound 10];

(11) N-benzenesulfonyl-L-tryptophane biphenylamide [referred to as compound 11];

(12) N-benzenesulfonyl-L-tyrosine biphenylamide [referred to as compound 12];

Exemplary 4-fluorobenzenesulfonylamide derivatives of the invention include:

(13) N-(4-fluorobenzenesulfonyl)-L-phenylalanine piperazineamide [referred to as compound 13];

(14) N-(4-fluorobenzenesulfonyl)-L-alanine piperazineamide [referred to as compound 14];

(15) N-(4-fluorobenzenesulfonyl)-L-valine piperazineamide [referred to as compound 15];

(16) N-(4-fluorobenzenesulfonyl)-L-proline piperazineamide [referred to as compound 16];

(17) N-(4-fluorobenzenesulfonyl)-L-phenylalanine biphenylamide [referred to as compound 17];

(18) N-(4-fluorobenzenesulfonyl)-L-alanine biphenylamide [referred to as compound 18];

(19) N-(4-fluorobenzenesulfonyl)-L-valine biphenylamide [referred to as compound 19];

(20) N-(4-fluorobenzenesulfonyl)-L-proline biphenylamide [referred to as compound 20];

Exemplary 5-chloro-1-naphthalenesulfonamide derivatives of the invention include:

(21) N-(5-chloro-1-naphthalenesulfonyl)-L-phenylalanine piperazineamide [referred to as compound 21];

(22) N-(5-chloro-1-naphthalenesulfonyl)-L-valine piperazineamide [referred to as compound 22];

(23) N-(5-chloro-1-naphthalenesulfonyl)-L-proline piperazineamide [referred to as compound 23];

(24) N-(5-chloro-1-naphthalenesulfonyl)-L-alanine piperazineamide [referred to as compound 24];

(25) N-(5-chloro-1-naphthalenesulfonyl)-L-phenylalanine-1,6-diaminohexaneamide [referred to as compound 25];

(26) N-(5-chloro-1-naphthalenesulfonyl)-L-phenylalanine biphenylamide [referred to as, compound 26];

(27) N-(5-chloro-1-naphthalenesulfonyl)-L-alanine biphenylamide [referred to as compound 27];

(28) N-(5-chloro-1-naphthalenesulfonyl)-L-valine biphenylamide [referred to as compound 28];

(29) N-(5-chloro-1-naphthalenesulfonyl)-L-proline biphenylamide [referred to as compound 29];

(30) N-biphenyl-5-chloro-1-naphthalenesulfonamide [referred to as compound 30];

Exemplary 5-isoquinolinesulfonylamide derivatives of the invention include:

(31) N-(5-isoquinolinesulfonyl)-L-phenylalanine piperazineamide [referred to as compound 31];

(32) N-(5-isoquinolinesulfonyl)-L-valine piperazineamide [referred to as compound 32];

(33) N-(5-isoquinolinesulfonyl)-L-proline piperazineamide [referred to as compound 33];

(34) N-(5-isoquinolinesulfonyl)-L-alanine piperazineamide [referred to as compound 34];

(35) N-(5-isoquinolinesulfonyl)-L-phenylalanine-1,6-diaminohexaneamide [referred to as compound 35];

(36) N-(5-isoquinolinesulfonyl)-L-phenylalanine biphenylamide [referred to as compound 36];

(37) N-(5-isoquinolinesulfonyl)-L-valine biphenylamide [referred to as compound 37];

(38) N-(5-isoquinolinesulfonyl)-L-proline biphenylamide [referred to as compound 38];

(39) N-(5-isoquinolinesulfonyl)-L-alanine biphenylamide [referred to as compound 39];

(40) N-(5-isoquinolinesulfonyl)-D-proline biphenylamide [referred to as compound 40];

(41) N-biphenyl-5-isoquinolinesulfonamide [referred to as compound 41];

(42) N-benzyl-5-isoquinolinesulfonamide [referred to as compound 42];

The acid addition salts of the derivatives 1–6, 13–16, 21–25 and 31–35 according to this invention are pharmaceutically acceptable non-toxic salts and can be prepared by conventional methods. Suitable examples of such pharmaceutically acceptable acid addition salts include the salts of inorganic acids such as hydrochloric acid, hydrobromic acid, phosphoric acid and sulfuric acid; and the salts of organic acids such as acetic acid, citric acid, tartaric acid, lactic acid, succinic acid, fumaric acid, maleic acid, methanesulfonic acid and p-toluenesulfonic acid.

The benzenesulfonamide—and the 4-fluorobenzenesulfonamide derivatives of formula I–II can be prepared in accordance with the following equations:

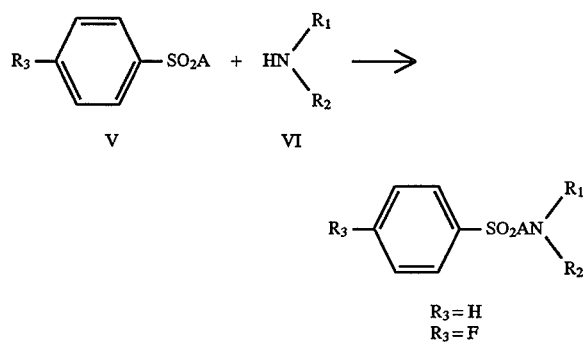

wherein A is a part of an amino acid, $R_1$ is a hydrogen atom, $R_2$ is a biphenyl group and $R_3$ is a hydrogen or a flourine atom;

or

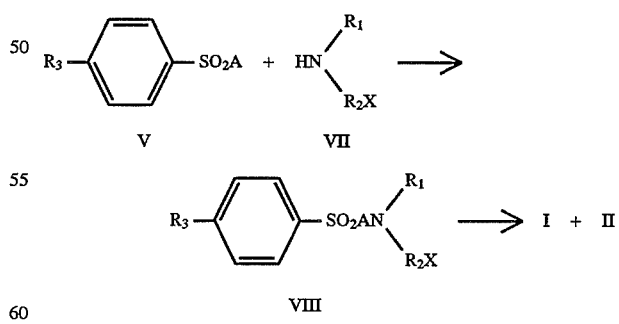

wherein A is a part of an amino acid, $R_1$ is a hydrogen atom and $R_2$ a $C_3$ or $C_6$ alkylene chain; or $R_1$ and $R_2$ are linked directly to form a piperazine ring. $R_3$ is a hydrogen or a flourine atom and X a protective group.

Derivative V can be prepared as follows:

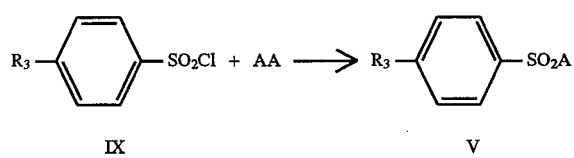

wherein AA is an amino acid and $R_3$ is a hydrogen or a flourine atom.

The naphthalenesulfonylamide derivatives of formula III can be prepared in accordance to the following equations:

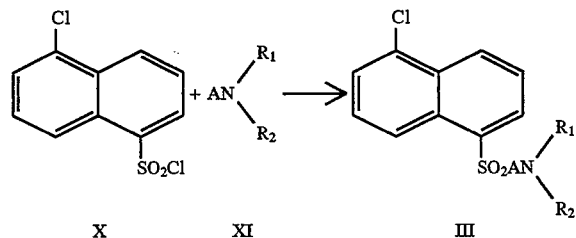

wherein A is a part of an amino acid or a single bond, $R_1$ is a hydrogen atom and $R_2$ is a biphenyl group; or

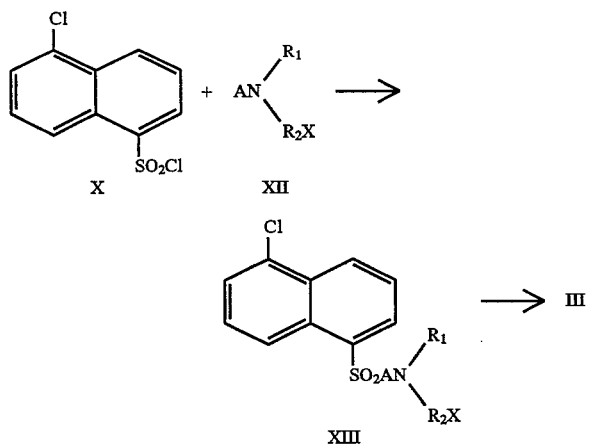

wherein A is a part of an amino acid, $R_1$ is a hydrogen atom and $R_2$ a $C_6$ alkylene chain; or $R_1$ and $R_2$ are linked directly to form a piperazine ring. X is a protective group.

Derivative XI can be prepared as follows:

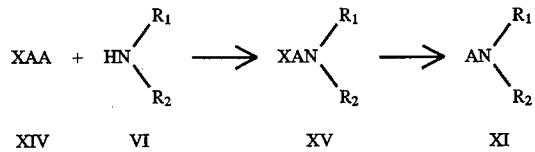

wherein AA is an amino acid, $R_1$ is a hydrogen atom, $R_2$ a biphenyl group and X a protective group.

Derivative XII can be prepared as follows:

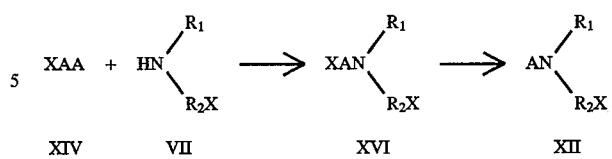

wherein AA is an amino acid, $R_1$ is a hydrogen atom and $R_2$ a $C_6$ alkylene chain; or $R_1$ and $R_2$ are linked directly to form a piperazine ring. X are protective groups.

The isoquinolinesulfonamide derivatives of formula IV can be prepared in accordance to the following equations:

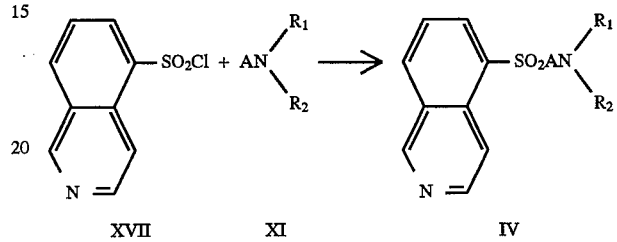

wherein A is a part of an amino acid or a single bond, $R_1$ is a hydrogen atom and $R_2$ a phenyl- or biphenyl group; or

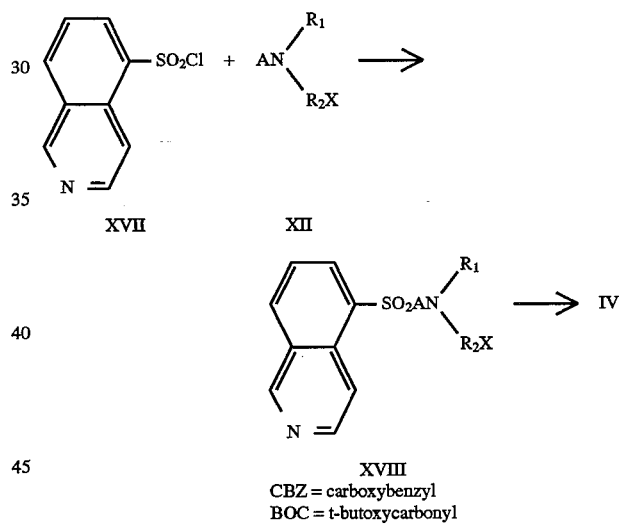

CBZ = carboxybenzyl
BOC = t-butoxycarbonyl wherein A is a part of an amino acid, $R_1$ is a hydrogen atom and $R_2$ a alkylene chain; or $R_1$ and $R_2$ are linked directly to form a piperazine ring. X is a protective group.

Exemplary compounds of formula V include N-benzenesulfonyl-L-phenylalanine, N-benzenesulfonyl-L-alanine, N-benzenesulfonyl-L-valine, N-benzenesulfonyl-L-proline, N-benzenesulfonyl-L-tryptophane and N-benzenesulfonyl-L-tyrosine; N-(4-fluorobenzenesulfonyl)-L-phenylalanine, N-(4-fluorobenzenesulfonyl)-L-alanine, N-(4-fluorobenzenesulfonyl)-L-valine, N-(4-fluorobenzenesulfonyl)-L-proline.

Exemplary compounds of formula VI include 4-aminobiphenyl and 4-aminobenzyl.

Exemplary compounds of formula VII include N-CBZ-piperazine, N-BOC-1,6-diaminohexane and N-CBZ-1,3-diaminopropane.

Exemplary compounds of formula XI include L-phenylalanine biphenylamide, L-alanine biphenylamide, L-valin biphenylamide, L-prolin biphenylamide and D-proline biphenylamide.

Exemplary compounds of formula XII include L-phenylalanine-N-CBZ-piperazineamide, L-alanine-N-CBZ-piperazineamide, L-valine-N-CBZ-piperazineamide and L-phenylalanine-N-BOC-1,6-diaminohexaneamide.

The reaction between the compound of formula V with the compound of formulae VI, or VII is best carried out in presence of dicyclohexylcarbodiimide (DCC) and a reaction medium like dimethylformamide (DMF) or dioxane; 1-hydroxybenzotriazole is used to avoid racemization.

The amount of the compound of formula V preferably is the same as of the compound of formula VI or VII.

The amount of DCC is preferably about 1 to 5 equivalents and more preferably 1 to about 2 equivalents for each mol of the compound of formulae V.

The amount of 1-hydroxybenzotriazole is preferably about 1 to 5 equivalents and more preferably 1 to about 2 equivalents for each mol of the compound of formulae V.

The reaction between the compound of formulae V with VI or VII, respectively, can be carried out typically at a temperature of about −10° C. to about 60° C. and preferably from about 0° C. to 30° C.

The reaction time which can be employed is typically about 1 h to about 24 h and preferably from 1 h to about 5 h.

The method of obtaining the compounds of formulae I and II from VIII may vary depending upon the protective group of X selected, generally known methods can be employed in this invention. For example when the protective group of X is an alkyloxycarbonyl group such as t-butoxycarbonyl, the desired products can be obtained by hydrolysis with an acid. When the promotive group of X is an arylmethyloxycarbonyl group such as benzyloxycarbonyl, the desired compounds can be obtained by hydrogenation or hydrolysis with an acid.

The reaction between the compound of formulae X with XI or XII respectively is best carried out in presence of an acid acceptor. Exemplary acid acceptors which can be employed include alkali metal compounds such as hydroxide, bicarbonate or carbonate, e.g. sodium hydroxide, potassium hydroxide, sodium bicarbonate, sodium carbonate, potassium carbonate and tertiary amines such as triethylamine and pyridine.

In general the reaction is carried out in presence of a reaction medium. Exemplary reaction media which can be employed include ethers, such as dioxane or THF and halogenated hydrocarbons such as $CHCl_3$ and $CH_2Cl_2$.

The amount of the compound of formula X preferably is the same as of the compounds of formula XI or XII.

The amount of the acid acceptor employed is preferably about 2 to 5 equivalents with more preferably about 2 to 3 equivalents for each mol of the compound of formulae X.

The reaction between the compound of formulae X with XI or XII respectively can be carried out typically at a temperature of about 10° C. to about 60° C. and preferably at 20° C. to 30° C.

The reaction time which can be employed is typically about 1 h to about 24 h and preferably from 1 h to about 5 h.

The method of obtaining the compound of formula III from XIII can be carried out under the same conditions as the reaction from the compound of formula VIII to the compound of formula I and II.

The reaction between the compound of formulae XVII or XI XII respectively can be carried out under the same condition as the reaction between the compound of formula X and XI respectively XII except that the amount of the compound of formula XVII preferably is 0.9 equivalents of the compound of formula XI respectively XII and that the reaction temperature is preferably of about 0° C. to 30° C.

It has now been found that the derivatives of formulae I–IV (and their pharmaceutically acceptable salts if applicable have pharmacologically and biochemically interesting properties such as Phospholipase $A_2$ ($PLA_2$) inhibition activity. The effect of the derivatives of formulae I–IV of this invention on $PLA_2$ can be proved in vitro by taking bovine pancreatic $PLA_2$, 1-stearoyl-2-[$C^{14}$]-arachidonyl-1-phosphatidylcholine and $CaCl_2$ and adding a derivative of the formulae I–V resulting in inhibition of the $PLA_2$. When for example N-(5-chloro-1-naphthalenesulfonyl)-L-phenylalanine-1,6-diaminohexaneamide, i.e. compound 25 was added and a complete inhibition was designed 100%, the concentration which would bring about an inhibition of 50%, i.e. $IC_{50}$ was 67 µM.

The following examples illustrate the present invention in more detail, but they are given for illustrative purposes only and are not to be construed as limiting the invention.

Synthesis of the Precursors

EXAMPLE 1

Equimolar amounts of O-benzyl-L-tyrosine and benzenesulfonyl chloride were mixed in 1N NaOH (200 mol %) and stirred for 2 h. After 0.5 h the desired compound precipitated. The solution was adjusted to pH 2 with 2N HCl and filtered. The precipitate was washed several times with $H_2O$, dried in vacuo over $P_2O_5$ and crystallized to yield the desired compound P1.

Substantially the used in place of described above was repeated except that L-tryptophane was used in place of the L-tyrosine derivative to give P2.

The yields of the reactions and the analytical data of the two compounds are given in table 1.

EXAMPLE 2

Equimolar mounts of L-phenylalanine and p-fluorobenzenesulfonyl chloride were mixed in 1N NaOH (200 mol %) and stirred at 60° C. for 2 h. The solution was adjusted to pH 2 with 2N HCl and extracted with EtOAc. The organic phase was dried over $MgSO_4$, filtered, evaporated and the residue crystallized to yield P3.

Substantially the same procedure as described above was repeated except that L-alanine (→P4), L-valine (→P5) and L-proline (→P6) were used in place of L-phenylalanine.

The yields of the reactions and the analytical data of the different compounds are given in table 1.

EXAMPLE 3

To equimolar amounts of N-t-BOC-L-phenylalanine and 4-aminobiphenyl in DMF (ca 0.5M) 1-hydroxybenzotriazole (150 mol %) was added. The mixture was cooled to 0° C. and DCC (110 mol %) was added in one portion. After stirring for 1 h at 0° C. and 1 h at 25° C. the reaction mixture was filtered and the DMF evaporated in vacuo. The residue was taken up in EtOAc (ca 0.1M) and washed subsequently with saturated $NaHCO_3$ solution, 2N citric acid and $H_2O$. After drying over $MgSO_4$, filtering and evaporation the residue was crystallized.

The compound obtained above was dissolved in $CH_2Cl_2$ (ca 0.4M) cooled with ice and the same amount of TFA added. After 1 h the solvents were evaporated and the residue crystallized: P7.

Substantially the same procedure as described above was repeated except that N-t-BOC-L-valine (→P8) was used in place of the L-phenylalanine derivative. When N-CBZ-L-proline was used as starting material the deprotection was done by overnight hydrogenation with $H_2$, 10% Pd/C in EtOH (→P9). In case of N-t-BOC-L-alanine the free amine was obtained after evaporation of the solvents and stirring the residue with saturated $NaHCO_3$ solution (→P10).

The yields of the reactions and the analytical data of the different compounds are given in table 2.

EXAMPLE 4

Basically the same procedure as in example 3 except that N-CBZ-piperazine [1] and N-BOC-6-aminohexane were used in place of 4-aminobiphenyl. In case of N-CBZ-piperazine N-t-BOC protected amino acids and in case of N-t-BOC-6-aminohexane N-CBZ protected amino acids were used.

Deprotection of the N-t-BOC group was done as described before with $TFA/CH_2Cl_2$ at 0° C. (→P11,P12, P13,P14) and of the N-CBZ group with $H_2$, 10% Pd/C in EtOH (→P15,P16). The free amine was dissolved in acetone, equimolar amounts of oxalic acid in acetone added, the precipitate filtered and crystallized.

The yields of the reactions and the analytical data of the different compounds are given in table 2.

Synthesis of the Compounds

EXAMPLE 5

To equimolar amounts of N-benzenesulfonyl-L-phenylalanine, [2] and N-CBZ-piperazine [1] in DMF (ca 0.5M) 1-hydroxybenzotriazole (150 mol %) was added. The mixture was cooled to 0° C. and DCC (110 mol %) was added in one portion. After stirring for 1 h at 0° C. and 1 h at 25° C. the reaction mixture was filtered and the DMF evaporated in vacuo. The residue was taken up in EtOAc (ca 0.1M) and washed subsequently with saturated $NaHCO_3$ solution, 2N citric acid and $H_2O$. After drying over $MgSO_4$, filtering and evaporation of the solvent the residue was crystallized (P17).

The compound obtained above was dissolved in abs. EtOH (ca 0.1M), 10% Pd/C (10 weight %) added and stirred overnight in a $H_2$ atmosphere. The reaction mixture was filtered over celite and the pH of the solution adjusted to 2 with conc. HCl. Evaporation of the solvent yielded a white residue which was crystallized: 1.

Substantially the same procedure as described above was repeated except that N-benzenesulfonyl-L-alanine [3](→2), N-benzenesulfonyl-L-valine [4](→P18 →3) and N-benzenesulfonyl-L-proline [5](→P19→4) were used in place of N-benzenesulfonyl-L-phenylalanine.

The yields of the reactions and the analytical data of the different compounds are given in table 3 (intermediates) and table 4 and 8 (compounds).

EXAMPLE 6

Basically the same procedure as in example 5 except that N-t-BOC-6-aminohexane (→P20→53) or N-CBZ-aminopropane [6](→P21→6) were used in place of N-CBZ-piperazine. Deprotection of the N-t-BOC group was done with $TFA/CH_2Cl_2$ at 0° C. and of the N-CBZ group with $H_2$, 10% Pd/C in EtOH as described before.

The yields of the reactions and the analytical data of the two compounds are given in table 3 (intermediates) and table 4 and 9 (compounds).

EXAMPLE 7

To equimolar mounts of N-benzenesulfonyl-L-phenylalanine [2] and 4-aminobiphenyl in DMF (ca 0.5M) 1-hydroxybenzotriazole (150 mol %) was added. The mixture was cooled to 0° C. and DCC (110 mol %) was added in one portion. After stirring for 1 h at 0° C. and 1 h at 25° C. the reaction mixture was filtered and the DMF evaporated in vacuo. The residue was taken up in EtOAc (ca 0.1M) and washed subsequently with saturated $NaHCO_3$ solution, 2N citric acid and $H_2O$. After drying over $MgSO_4$, filtering and evaporation of the solvent the residue was crystallized: 7.

Substantially the same procedure as described above was repeated except that N-benzenesulfonyl-L-alanine [3](→8), N-benzenesulfonyl-L-valine [4](→9), N-benzenesulfonyl-L-proline [5](→10) and N-benzenesulfonyl-L-tryptophane P2 (→11) were used in place of N-benzenesulfonyl-L-phenylalanine.

The yields of the reactions and the analytical data of the different compounds are given in table 4,10,11 and 12.

EXAMPLE 8

Basically the same procedure as in example 7 except that O-benzyl-N-benzenesulfonyl-L-tyrosine P1 was used in place of N-benzenesulfonyl-L-phenylalanine (→P22).

The compound obtained above was dissolved in p-dioxane/$H_2O$/HOAc 15:1:1 (ca 10 mM), 10% Pd/C (10 weight %) added and the mixture stirred overnight in a $H_2$ atmosphere. The reaction mixture was filtered over celite and the solvents evaporated in vacuo. The residue was crystallized: 12.

The yields of the reactions and the analytical data of the two compounds are given in table 3 (intermediate) and table 4 and 10 (compound).

EXAMPLE 9

To equimolar amounts of N-p-fluorobenzenesulfonyl-L-phenylalanine P3 and N-CBZ-piperazine in DMF (ca 0.5M) 1-hydroxybenzotriazole (150 mol %) was added. The mixture was cooled to 0° C. and DCC (110 mol %) was added in one portion. After stirring for 1 h at 0° C. and 1 h at 25° C. the reaction mixture was filtered and the DMF evaporated in vacuo. The residue was taken up in EtOAc (0.1M) and washed subsequently with saturated $NaHCO_3$ solution, 2N citric acid and $H_2O$. After drying over $MgSO_4$, filtering and evaporation of the solvent the residue was crystallized: P23.

The compound obtained above was dissolved in abs. EtOH (ca 0.1M) 10% Pd/C (10 weight %) added and the mixture stirred overnight in a $H_2$ atmosphere. The reaction mixture was filtered over celite and the pH of the solution adjusted to 2 with conc. HCl. Evaporation of the solvent yielded a white residue which was crystallized: 13.

Substantially the same procedure as described above was repeated except that N-p-fluorobenzenesulfonyl-L-alanine P4 (→P24→14), N-p-fluorobenzenesulfonyl-L-valine P5 (→P25→15) and N-p-fluorobenzenesulfonyl-L-proline P6 (→P26→16) were used in place of P3.

The yields of the reactions and the analytical data of the different compounds are given in table 3 (intermediates) and 5 and 13 (compounds).

EXAMPLE 10

To equimolar amounts of N-p-fluorobenzenesulfonyl-L-phenylalanine P3 and 4-aminobiphenyl in DMF (ca 0.5M) 1-hydroxybenzotriazole (150 mol %) was added. The mixture was cooled to 0° C. and DCC (110 mol %) was added, in one portion. After stirring for 1 h at 0° C. and 1 h at 25° C. the reaction mixture was filtered and the DMF evaporated in vacuo. The residue was taken up in EtOAc (ca 0.1M) and washed subsequently with saturated NaHCO$_3$ solution, 2N citric acid and H$_2$O. After drying over MgSO$_4$, filtering and evaporation of the solvent the residue was crystallized: 17.

Substantially the same procedure as described above was repeated except that N-p-fluorobenzenesulfonyl-L-alanine P4 (→18), N-p-fluorobenzenesulfonyl L-valine P5 (→19) and N-p-fluorobenzenesulfonyl L-proline P6 (→20) were used in place of P3.

The yields of the reactions and the analytical data of the different compounds are given in table 5 and 14.

EXAMPLE 11

To a concentrated solution of the amine P11 in p-dioxane and 1N NaOH (200 mol %) an equimolar amount of 5-chloro-1-naphthalenesulfonyl chloride [7,8] was added and the suspension stirred for 3 h. Acidification with conc. HCl to pH 2, extraction with CH$_2$Cl$_2$ (3x), washing of the organic phase once with brine, drying over MgSO$_4$, filtering and evaporation of the solvents in vacuo yielded a residue which was purified by flash chromatography on silica gel (solvent system hexane/EtOAc 1:1).

The compound obtained above was dissolved in abs. EtOH (ca 50 mM) 10% Pd/C (10 weight %) added and the mixture stirred for 3 days in a H$_2$ atmosphere. The reaction mixture was filtered over celite, the solvent evaporated in vacuo, the residue purified by flash chromatography on silica gel (solvent system CH$_2$Cl$_2$/MeOH 5:1) and crystallized: 21.

Substantially the same procedure as described above was repeated except that the amine P12 (→22)[2], P13 (→23)[3] or P14 (→24)[4] were used in place of the amine P11.

[2] Solvent system for the intermediate: hexane/EtOAc 1:1; no chromatography was necessary for 22.

[3] Solvent system for the intermediate: hexane/EtOAc 1:2; solvent system for 23: CH$_2$Cl$_2$/MeOH 10:3.

[4] Solvent system for the intermediate hexane/EtOAc 1:2; no chromatography was necessary for 24.

The yields of the reactions and the analytical data of the different compounds are given in table 6 and 15.

EXAMPLE 12

To a concentrated solution of the amine P15 in p-dioxane and 1N NaOH (200 mol %) an equimolar amount of 5-chloro-1-naphthalenesulfonyl chloride was added and the suspension stirred for 3 h. H$_2$O was added and the mixture extracted thrice with CH$_2$Cl$_2$. The organic phase was washed once with H$_2$O, dried over MgSO$_4$, filtered and the solvents evaporated in vacuo. Flash chromatography on silica gel (solvent system hexane/EtOAc 1:2) yielded the pure intermediate which was dissolved in CH$_2$Cl$_2$ (ca 50 mM) and the same volume of TFA added. After 1 h the solvents were evaporated in vacuo, the residue dissolved in a small volume of H$_2$O and the pH of the solution adjusted to 8 with solid NaHCO$_3$. Extraction with four portions of CH$_2$Cl$_2$/MeOH 3:1, washing of the organic phase with H$_2$O, drying over MgSO$_4$, filtering and evaporation of the solvents in vacuo yielded a compound which was purified by flash chromatography on silica gel (solvent system CH$_2$Cl$_2$/MeOH/conc.NH$_3$ 20:2:1) and crystallized as HCl-salt 25.

The yield of the reaction and the analytical data of the compound are given in table 6 and 16.

EXAMPLE 13

To a concentrated solution of the amine P7 in THF and 1N NaOH (200 mol %) an equimolar amount of 5-chloro-1-naphthalenesulfonyl chloride was added and the suspension stirred for 3 h. H$_2$O was added and the mixture extracted thrice with CH$_2$Cl$_2$. The organic phase was washed once with H$_2$O, dried over MgSO$_4$, filtered and the solvents evaporated in vacuo. Flash chromatography on silica gel (solvent system hexane/EtOAc 4:1) and crystallization yielded the pure compound 26.

Substantially the same procedure as described above was repeated except that the amine P10 (→27)[5] was used in place of the amine P7.

[5] Solvent system for 27: hexane/EtOAc 2:1.

The yields of the reactions and the analytical data of the two compounds are given in table 6 and 17.

EXAMPLE 14

To a concentrated solution of the amine P8 in p-dioxane was added 1N NaOH (200 mol %). The precipitate partly dissolved after addition of a concentrated solution of an equimolar mount of 5-chloro-1-naphthalenesulfonyl chloride in THF. After 15 min. the desired compound precipitated. After 2 h H$_2$O was added and the suspension filtered, the solid dried and crystallized twice to obtain the pure compound 28.

Substantially the same procedure as described above was repeated except that the amine P9 (→29) was used in place of the amine P8.

The yields of the reactions and the analytical data of the two compounds are given in table 6 and 17.

EXAMPLE 15

To a concentrated solution of 4-aminobiphenyl in p-dioxane was added 1N NaOH (200 mol %) and an equimolar amount of 5-chloro-1-naphthalenesulfonyl chloride. After stirring for 2 h the solvents were evaporated in vacuo. The residue was purified by flash chromatography on silica gel (solvent system hexane/EtOAc 2:1) and crystallized to yield 30.

The yield of the reaction and the analytical data of the compound are given in table 6 and 17.

EXAMPLE 16

To an ice cooled suspension of 5-isoquinolinesulfonyl chloride hydrochloride [9] in CH$_2$Cl$_2$ was added NEt$_3$ (220 mol %). To the yellow solution the amine P11 (90 mol %) in CH$_2$Cl$_2$ was added dropwise. After 10 min. the cooling was removed and the stirring continued for 2 h. The pH of the solution was adjusted to 7–8 with a saturated NaHCO$_3$ solution. The phases were separated and the organic phase washed once with H$_2$O, dried over MgSO$_4$, filtered and the solvent evaporated in vacuo. Flash chromatography on silica gel (solvent system CH$_2$Cl$_2$/MeOH 100:3) yielded a white foam.

A solution of the compound obtained above in 25% HBr/HOAc (8 ml/mmol) was stirred under ice cooling for 5 h. After addition of Et$_2$O (ca 40 ml/mmol the precipitate was filtered and dissolved in a few ml of H$_2$O. The solution was slightly basified with 1N NaOH and extracted with CH$_2$Cl$_2$/MeOH 3:1 (4x). The organic phase was washed once with H$_2$O, dried over MgSO$_4$, filtered and the solvents evaporated in vacuo. Flash chromatography on silica gel (solvent system CH$_2$Cl$_2$/MeOH/conc. NH$_3$ 20:4:1) yielded a foam which was dissolved in EtOH and treated with conc. HCl to give the salt 31.

Substantially the same procedure as described above was repeated except that the amine P12 (→32)[6,7] P13 (→33) and P14 (→34)[8,9] were used in place of the amine P11.

[6] Solvent system for the intermediate: CH₂Cl₂/MeOH 100:4.
[7] 32 in EtOH was nested with conc. HCl. The precipitate was filtered and thoroughly washed with EtOH. The salt could not be crystallized.
[8] Solvent system for the intermediate: CH₂Cl₂/MeOH 100:5.
[9] 34 was not purified by flash chromatography but directly crystallized as HCl-salt.

The yields of the reactions and the analytical data of the different compounds are given in table 7 and 18.

EXAMPLE 17

To an ice cooled suspension of 5-isoquinolinesulfonyl chloride hydrochloride in CH₂Cl₂ was added NEt₃ (220 mol %). To the yellow solution the amine P15 (90 mol %) in CH₂C₂ was added dropwise. After 10 min. the cooling was removed and stirring continued for 2 h. A saturated NaHCO₃ solution was added to adjust the pH to 7–8. The phases were separated and the organic phase washed once with H₂O, dried over MgSO₄, filtered and the solvent evaporated in vacuo. The residue was purified by flash chromatography on silica gel (solvent system CH₂Cl₂/MeOH 100:4).

To the compound obtained above, dissolved in CH₂Cl₂ (ca 50 mM), the same volume of TFA was added. After 1 h the solvents were evaporated in vacuo, the residue dissolved in a very small volume of H₂O and the pH of the solution adjusted to 8 with solid NaHCO₃. The H₂O phase was extracted with CH₂Cl₂/MeOH 3:1 (4x). The organic phase was dried over MgSO₄, filtered and evaporated to dryness. The residue was purified by flash chromatography on silica gel (solvent system CH₂Cl₂/MeOH/conc. NH₃ 20:4:1) and crystallized as HCl-salt 35.

The yield of the reaction and the analytical data of the compound are given in table 7 and 16.

EXAMPLE 18

To an ice cooled suspension of 5-isoquinolinesulfonyl chloride hydrochloride in CH₂Cl₂ was added NEt₃ (220 mol %). To the yellow solution the amine P7 (90 mol %) was added dropwise. After 10 min. the cooling was removed and stirring continued for 2 h. The pH of the solution was adjusted to 7–8 with a saturated NaHCO₃ solution. The phases were separated and the organic phase washed once with H₂O, dried over MgSO₄, filtered and the solvent evaporated in vacuo. Flash chromatography on silica gel (solvent system CH₂Cl₂/MeOH 100:3) yielded a white solid which was crystallized to give 36.

Substantially the same procedure as described above was repeated except that the amine P8 (→37), P9 (→38)[10], P10 (→39)[11] and (+)-P9 (→40) were used in place of the amine P7.
[10] Solvent system for 38 and 40: CH₂Cl₂/MeOH 100:2.
[11] Solvent system for 39: CH₂Cl₂/MeOH 100:5.

The yields of the reactions and the analytical data of the different compounds are given in table 7 and 19.

EXAMPLE 19

Substantially the same procedure as described in example 18 was used except that 4-aminobiphenyl (→41)[12] and 4-aminobenzol (→42) were used in place of the amine P7.
[12] Solvent system for 41 and 42: CH₂Cl₂/MeOH 100:2.

The yields of the reaction and the analytical data of the two compounds are given in table 7 and 19.

Enzyme Assay

Phospholipase A₂ (PLA₂) activity was measured using bovine pancreatic PLA₂ as the enzyme and a sonicated dispersion of 1-stearoyl-2-[C¹⁴]-arachidonyl-phosphatidylcholine (56 mCi/mmol) as the substrate in the following manner [11,12]: 60 ng bovine pancreatic PLA₂ was mixed and incubated with buffer and inhibitors (100 mM Tris, pH 8; 100 mM CaCl₂; 20 mM EDTA, pH 8) at 37° C. for 10 min. to allow interaction between the enzyme and the drugs. The substrate (38 nCi) in buffer and 0.3% cholate was added to initiate the reaction which continued for 20 min. at 37° C. The total reaction volume was 0.1 ml. The reaction was stopped by adding 0.1 ml of an ice cold EtOH/HOAc 98:2 mixture. Released arachidonic acid was separated from the unreacted substrate via thin layer chromatography on silica gel (solvent system CHCl₃/MeOH/H₂O 14:6:1). The radioactivity of the two spots was quantified using a bioscanner.

Inhibitors were dissolved in buffer[13] and tested in duplicate within each experiment, and each inhibitor was tested in at least two experiments. When necessary, inhibitors were dissolved in DMSO[14]. The % inhibition at a given concentration was combined for several experiments and the IC₅₀ determined from a semilog plot of % inhibition vs concentration. Under the condition described the rate of hydrolysis was 20–25% of the substrate being hydrolyzed in absence of inhibitors. The results are listed in table 20.
[13] 0.01 ml inhibitor solution were used in these experiments.
[14] 0.005 ml inhibitor solution were used in these experiments (=5 vol %).

TABLE 1

| Structure | mp, [°C.] (cryst. from) | $[\alpha]_D^{20}$, [°] | yield [%] | analysis | MS, m/e [%] | ID |
|---|---|---|---|---|---|---|
| (phenyl-SO₂-)(---HN,,,CO₂H / H)(CH₂-C₆H₄-OBn) | 150–151 (EtOH) | +0.27 (c = 1.11, acetone) | 63.5 | C₂₂H₂₁NO₅S *0.5 H₂O *0.5 EtOH (C,H,N) | 411 (49) | P1 |
| ----HN,CO₂H / H, (indole-CH₂-) | 153–154 (EtOH) | +36.5 (C = 1.07, DMSO) | 50.1 | C₁₇H₁₆N₂O₄S | 344 (27) | P2 |

TABLE 1-continued

| | | mp, [°C.] (cryst. from) | $[\alpha]_D^{20}$, [°] | yield [%] | analysis | MS, m/e [%] | ID |
|---|---|---|---|---|---|---|---|
| 4-F-C6H4-SO2— | —HN⸝⸝CO2H, H, CH2Ph | 118–119 (Et2O, pet. ether) | +5.8 (c = 1.18, EtOH) | 57.8 | $C_{15}H_{14}FNO_4S$ (C,H,N) | 323 (0.1) | P3 |
| | —HN⸝⸝CO2H, H, CH3 | 109–110 (Et2O, pet. ether) | −3.9 (c = 1.42, EtOH) | 58.9 | $C_9H_{10}FNO_4S$ (C,H,N) | 247 (0.1) | P4 |
| | —HN⸝⸝CO2H, H, iPr | 126–127 (Et2O, pet. ether) | +23.1 (c = 1.43, EtOH) | 64.5 | $C_{11}H_{14}FNO_4S$ (C,H,N) | 275 (1) | P5 |
| | pyrrolidine-N, CO2H | 116–117 (Et2O, pet. ether) | −81.9 (c = 1.5, EtOH) | 77.3 | $C_{11}H_{12}FNO_4S$ (C,H,N) | 273 (0.1) | P6 |

TABLE 2

| | | R | mp, [°C.] (cryst. from) | $[\alpha]_D^{20}$, [°] | yield [%] |
|---|---|---|---|---|---|
| RHN⸝⸝CO—, H, CH2Ph | —HN—C6H4—C6H5 | BOC | 186–187 (acetone) | −6.9 (c = 0.62, CHCl3) | 66.4 |
| RHN⸝⸝CO—, H, iPr | | H | 213–214 (acetone, Et2O, pet. ether) | +15.1 (c = 0.69, acetone) | 72.5 |
| RHN⸝⸝CO—, H, iPr | | BOC | 180–182 (EtOAc, hexane) | −33.3 (c = 0.91, CHCl3) | 58.3 |
| | | H | 190–191 (EtOH, pet. ether) | −71.4 (c = 0.57, acetone) | 67.5 |
| pyrrolidine RN-CO— | | H | 156–157 (EtOH) | −54.0 (c = 0.79, CHCl3) | 54.7 |
| RHN⸝⸝CO—, H, CH3 | | BOC | 159–160 (EtOAc) | −63.1 (c = 1.1, CHCl3) | 69.6 |
| | | H | 217–218 (MeOH) | +7.5 (c = 0.27, DMSO) | 100 |
| RHN⸝⸝CO—, H, CH2Ph | —N(piperazine)NCBZ | H | 181–183 (EtOH) | +26.9 (c = 0.525, DMSO) | 58.1 |
| RHN⸝⸝CO—, H, iPr | | BOC | 104–105 (acetone, pet. ether) | +27.1 (c = 0.95, CHCl3) | 65.1 |
| | | H | 153–154 (acetone) | +17.3 (c = 1.04, H2O) | 78.2 |

TABLE 2-continued

| Structure (amino acid) | Substituent | R | mp (°C) (solvent) | [α] (c, solvent) | yield % |
|---|---|---|---|---|---|
| pyrrolidine (RN, CO) | | BOC | 109–110 (acetone, pet. ether) | −9.7 (c = 0.65, CHCl₃) | 84.6 |
| | | H | 141–142 (EtOH) | −21.6 (C = 0.58, acetone) | 81.3 |
| Ala (RHN, CO, CH₃) | | H | 193–194 (MeOH) | +4.9 (c = 0.88, DMSO) | 79.7 |
| Phe (RHN, CO, CH₂Ph) | ...HN(CH₂)₆NHBOC | CBZ | 126–127 (acetone) | +4.5 (c = 1.15, CHCl₃) | 57.4 |
| | | H | 142–143 (EtOH) | +31.9 (c = 0.74, MeOH) | 100 |
| pyrrolidine (RN, CO) | | CBZ | 95–96 (acetone) | −56.9 (c = 1.2, CHCl₃) | 67.7 |
| | | H | 163–164 (EtOH) | −25.1 (c = 0.71, DMSO) | 85.0 |

| Structure | Substituent | analysis | MS, m/e [%] | ID |
|---|---|---|---|---|
| Phe (RHN, CO, CH₂Ph) | ---HN-biphenyl | $C_{26}H_{28}N_2O_3$ (C,H,N) | 416 (24) | |
| | | $C_{21}H_{20}N_2O$ *$CF_3COOH$ (C,H,N) | 316 (9) | P7 |
| Val (RHN, CO, iPr) | | $C_{22}H_{28}N_2O_3$ (C,H,N) | 368 (0.2) | |
| | | $C_{17}H_{20}N_2O$ *$CF_3COOH$ (C,H,N) | 268 (10) | P8 |
| pyrrolidine (RN, CO) | | $C_{17}H_{18}N_2O$ | 266 (42) | P9 |
| Aib (RHN, CO, (CH₃)₂) | | $C_{20}H_{24}N_2O_3$ (C,H,N) | 340 (0.2) | |
| | | $C_{15}H_{16}N_2O$ *(COOH)₂*0.25 MeOH (C,H,N) | 240 (13) | P10 |
| Phe (RHN, CO, CH₂Ph) | ---N(piperazine)NCBZ | $C_{21}H_{25}N_3O_3$ *0.75 (COOH)₂ (C,H,N) | 367 (0.1) | P11 |
| Val (RHN, CO, iPr) | | $C_{22}H_{33}N_3O_5$ (C,H,N) | 419 (0.1) | |
| | | $C_{17}H_{25}N_3O_3$ | | P12 |

TABLE 2-continued

| Structure | Formula | Code / MS |
|---|---|---|
| (pyrrolidine with RN, CO) | *0.5(COOH)₂ C₂₂H₃₁N₃O₅ (C,H,N) | 417 (0.3) |
| | C₁₇H₂₃N₃O₃ *(COOH)₂ (C,H,N) | P13 |
| RHN-CH(CH₃)-CO | C₁₅H₂₁N₃O₃ *(COOH)₂ (C,H,N) | P14 |
| RHN-CH(CH₂Ph)-CO | C₂₈H₃₉N₃O₅ (C,H,N) | 497 (0.1) |
| | C₂₀H₃₃N₃O₃ *(COOH)₂*0.3 H₂O (C,H,N) | P15 |
| (pyrrolidine with RN, CO) | C₂₄H₃₇N₃O₅ (C,H,N) | 447 (0.2) |
| | C₁₆H₃₁N₃O₃ *(COOH)₂ (C,H,N) | P16 |

TABLE 3

| | | | mp, [°C.] (cryst. form) | $[\alpha]_D^{20}$, [°] |
|---|---|---|---|---|
| PhSO₂— | —HN-CH(CH₂Ph)-CO— | —N(piperazine)NCBZ | 116–117 (EtOH, pet. ether) | +81.2 (c = 1.08, CHCl₃) |
| | —HN-CH(iPr)-CO— | | 119–120 (EtOH) | +77.6 (c = 1.0, CHCl₃) |
| | (pyrrolidine N, CO) | | 158–160 (EtOH) | −29.0 (c = 1.0, CHCl₃) |
| | —HN-CH(CH₂Ph)-CO— | ...HN(CH₂)₆NHBOC | 154–155 (acetone) | +18.0 (c = 0.56, DMSO) |
| | | ...HN(CH₂)₃NHCBZ | 135–136 (acetone, pet. ether) | −24.7 (c = 0.785, CHCl₃) |
| | —HN-CH(CH₂-C₆H₄-OBn)-CO— | ...HN-C₆H₄-C₆H₅ | 211–212 (acetone) | +81.9 (c = 0.81, DMSO) |

TABLE 3-continued

| R₁ | R₂ | R₃ | mp (°C) (solvent) | [α] (c, solvent) |
|---|---|---|---|---|
| 4-F-C₆H₄-SO₂- | -HN-CH(CH₂Ph)-CO- | -N(piperazine)NCBZ | 104–105 (EtOH, pet. ether) | +73.0 (c = 1.22, CHCl₃) |
|  | -HN-CH(CH₃)-CO- |  | 97–98 (EtOH, pet. ether) | +36.8 (c = 0.86, CHCl₃) |
|  | -N-pyrrolidine-CO- |  | 156–157 (EtOH) | −12.0 (C = 1.4, CHCl₃) |
|  | -HN-CH(iPr)-CO- |  | 102–103 (t-amylalcohol) | +63.7 (c = 0.56, DMSO) |

| R₁ | R₂ | R₃ | yield [%] | analysis | MS, m/e [%] | ID |
|---|---|---|---|---|---|---|
| C₆H₅-SO₂- | -HN-CH(CH₂Ph)-CO- | -N(piperazine)NCBZ | 82.0 | C₂₇H₂₉N₃O₅S (C,H,N) | 507 (1) | P17 |
|  | -HN-CH(iPr)-CO- |  | 81.0 | C₂₃H₂₉N₃O₅S (C,H,N) | 459 (1) | P18 |
|  | -N-pyrrolidine-CO- |  | 44.0 | C₂₃H₂₇N₃O₅S (C,H,N) | 457 (1) | P19 |
|  | -HN-CH(CH₂Ph)-CO- | ...HN(CH₂)₆NHBOC | 81.5 | C₂₆H₃₇N₃O₅S (C,H,N) | 503 (6) | P20 |
|  |  | ...HN(CH₂)₃NHCBZ | 59.0 | C₂₆H₂₉N₃O₅S (C,H,N) | 495 (0.1) | P21 |
|  | -HN-CH(CH₂-C₆H₄-OBn)-CO- | ...HN-C₆H₄-C₆H₅ | 59.9 | C₃₄H₃₀N₂O₄S (C,H,N) | 562 (12) | P22 |
| 4-F-C₆H₄-SO₂- | -HN-CH(CH₂Ph)-CO- | -N(piperazine)NCBZ | 86.1 | C₂₇H₂₈FN₃O₅S (C,H,N) | 525 (0.3) | P23 |
|  | -HN-CH(CH₃)-CO- |  | 79.7 | C₂₁H₂₄FN₃O₅S *0.5 C₆H₁₄ (C,H,N) | 449 (4) | P24 |
|  | -N-pyrrolidine-CO- |  | 66.5 | C₂₃H₂₆FN₃O₅S (C,H,N) | 475 (0.1) | P25 |

TABLE 3-continued
| | | | | |
|---|---|---|---|---|
| 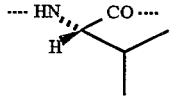 | 71.0 | $C_{23}H_{28}FN_3O_5S$ *0.25 t-amyl-alcohol (C,H,N) | 477 (28) | P26 |
TABLE 4
| | | | mp, [°C.] (cryst. from) | $[\alpha]_D^{20}$, [°] | yield [%] |
|---|---|---|---|---|---|
| 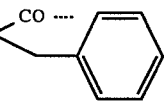 | 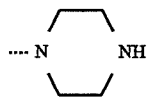 | 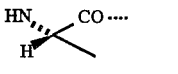 | 231–233 (MeOH, Et₂O) | +63.3 (c = 2.095, H₂O) | 81.5 |
| | 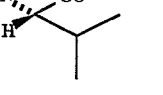 | | 203–204 (EtOH, Et₂O) | −4.7 (c = 0.725, H₂O) | 80.1 |
| |  | | 248–250 (EtOH, Et₂O) | +34.3 (c = 1.515, H₂O) | 58.1 |
| | 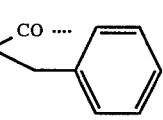 | | 282–284 dec (EtOH) | −135.6 (c = 1.72, H₂) | 78.8 |
| |  | ...HN(CH₂)₆NH₂ | 123–124 (MeOH, Et₂O) | +0.1 (c = 0.955, H₂O) | 81.0 |
| | | ...HN(CH₂)₃NH₂ | 150–152; sinters at ca 80° (amorphous) | −42.6 (c = 0.655, EtOH) | 81.0 |
| 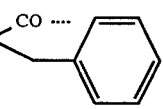 | 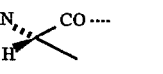 | 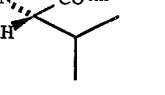 | 200–202 (EtOH) | +15.4 (c = 0.62, acetone) | 72.4 |
| | 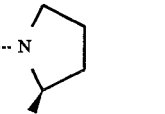 | | 178–180 (EtOH) | −75.6 (c = 0.6, acetone) | 55.5 |
| | 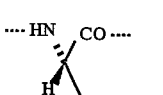 | | 226–227 (EtOH) | −12.7 (c = 0.94, acetone) | 54.4 |
| | 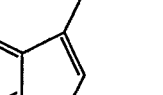 | | 212–214 (EtOH) | −224.0 (c = 0.26, acetone) | 62.9 |
| |  | | 219–221 (EtOH) | +73.4 (c = 0.56, DMSO) | 51.1 |

TABLE 4-continued
| | | | | | |
|---|---|---|---|---|---|
| | 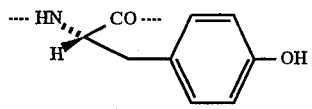 | | 222–223 (EtOH) | +92.3 (c = 1.23, DMSO) | 65.1 |
| | | | analysis | MS, m/e [%] | ID |
|---|---|---|---|---|---|
| 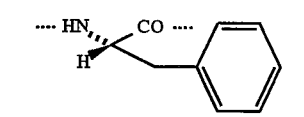 | 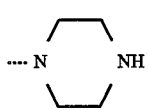 | 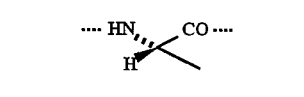 | $C_{19}H_{23}N_3O_2S*HCl$ (C,H,N) | | 1 |
| | 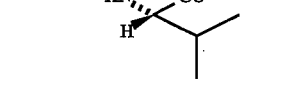 | | $C_{13}H_{19}N_3O_2S*HCl$ *0.25 $H_2O$ (C,H,N) | | 2 |
| |  | | $C_{15}H_{23}N_3O_2S*HCl$ (C,H,N) | | 3 |
| | 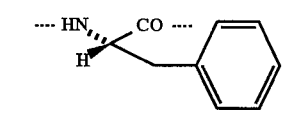 | | $C_{15}H_{21}N_3O_2S*HCl$ (C,H,N) | | 4 |
| | 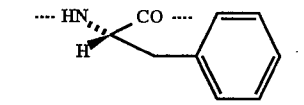 | ...HN($CH_2H_5NH_2$ | $C_{21}H_{29}N_3O_2S*HCl$ (C,H,N) | | 5 |
| | | ...HN($CH_2$)$_3NH_2$ | $C_{18}H_{23}N_3O_3S*HCl$ (C,H,N) | | 6 |
| 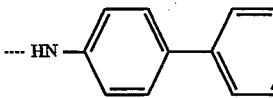 | 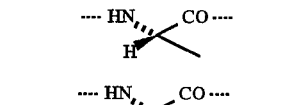 | 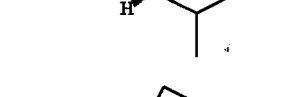 | $C_{27}H_{24}N_2O_3S$ (C,H,N) | 456 (39) | 7 |
| | 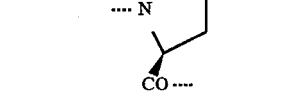 | | $C_{21}H_{20}N_2O_3S$ (C,H,N) | 380 (29) | 8 |
| | 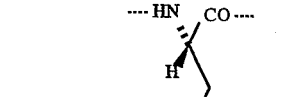 | | $C_{23}H_{24}N_2O_3S$ (C,H,N) | 408 (28) | 9 |
| | 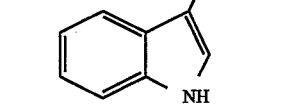 | | $C_{23}H_{22}N_2O_3S$ (C,H,N) | 406 (14) | 10 |
| | 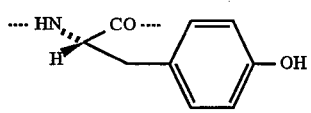 | | $C_{29}H_{25}N_3O_3S$ (C,H,N) | 495 (74) | 11 |
| |  | | $C_{27}H_{24}N_2O_4S$ *0.25 EtOH (C,H,N) | 472 (53) | 12 |

TABLE 5

| R1 | R2 | R3 | mp, [°C.] (cryst. from) | $[\alpha]_D^{20}$, [°] | yield [%] |
|---|---|---|---|---|---|
| 4-F-C6H4-SO2- | -HN-CH(CH2Ph)-CO- | piperazine (-N...NH) | 227–229 (MeOH, Et2O) | +44.0 (c = 1.65, H2O) | 51.0 |
| 4-F-C6H4-SO2- | -HN-CH(CH3)-CO- | piperazine | 218–219 (EtOH, Et2O) | −15.8 (c = 1.16, H2O) | 51.0 |
| 4-F-C6H4-SO2- | -HN-CH(iPr)-CO- | piperazine | 194–195 (MeOH, Et2O) | +19.5 (c = 1.24, H2O) | 60.4 |
| 4-F-C6H4-SO2- | pyrrolidine-2-CO- | piperazine | 278–280 (EtOH) | −127.6 (c = 1.36, H2O) | 87.6 |
| 4-F-C6H4-SO2- | -HN-CH(CH2Ph)-CO- | -HN-C6H4-C6H5 (4-biphenylamino) | 179–180 (EtOH) | +27.0 (c = 1.42, acetone) | 68.4 |
| 4-F-C6H4-SO2- | -HN-CH(CH3)-CO- | -HN-C6H4-C6H5 | 220–222 (EtOH) | −63.7 (c = 0.765, acetone) | 67.6 |
| 4-F-C6H4-SO2- | -HN-CH(iPr)-CO- | -HN-C6H4-C6H5 | 243–244 (EtOH) | −1.9 (c = 1.035, acetone) | 51.5 |
| 4-F-C6H4-SO2- | pyrrolidine-2-CO- | -HN-C6H4-C6H5 | 219–220 (EtOH) | −182.7 (c = 1.55, acetone) | 52.1 |

| R1 | R2 | R3 | analysis | Ms, m/e [%] | ID |
|---|---|---|---|---|---|
| 4-F-C6H4-SO2- | -HN-CH(CH2Ph)-CO- | piperazine | $C_{19}H_{22}FN_3O_3S \cdot HCl$ (C,H,N) | | 13 |
| 4-F-C6H4-SO2- | -HN-CH(CH3)-CO- | piperazine | $C_{13}H_{18}FN_3O_3S \cdot HCl$ (C,H,N) | | 14 |
| 4-F-C6H4-SO2- | -HN-CH(iPr)-CO- | piperazine | $C_{15}H_{22}FN_3O_3S \cdot HCl \cdot 0.5\, MeOH$ (C,H,N) | | 15 |
| 4-F-C6H4-SO2- | pyrrolidine-2-CO- | piperazine | $C_{15}H_{20}FN_3O_3S \cdot HCl$ (C,H,N) | | 16 |
| 4-F-C6H4-SO2- | -HN-CH(CH2Ph)-CO- | -HN-C6H4-C6H5 | $C_{27}H_{23}FN_2O_3S$ (C,H,N) | 474 (67) | 17 |
| 4-F-C6H4-SO2- | -HN-CH(CH3)-CO- | -HN-C6H4-C6H5 | $C_{21}H_{19}FN_2O_3S$ (C,H,N) | 398 (14) | 18 |

TABLE 5-continued

| | | | |
|---|---|---|---|
| ⋯⋯HN⎯CH(CH(CH₃)₂)⎯CO⋯⋯ | | C₂₃H₂₃FN₂O₃S (C,H,N) | 426 (41) | 19 |
| pyrrolidine-2-CO⋯⋯ with ⋯⋯N | | C₂₃H₂₁FN₂O₃S (C,H,N) | 424 (22) | 20 |

TABLE 6

| | | | mp, [°C.] (cryst. from) | [α]$_D^{20}$, [°] | yield [%] |
|---|---|---|---|---|---|
| 5-Cl-naphthalene-1-SO₂⋯⋯ | ⋯⋯HN⎯CH(CH₂Ph)⎯CO⋯⋯ | piperazine (⋯⋯N⎯NH) | 229–230 dec (t-amylalcohol) | −84.1 (c = 0.31, H₂O) | 25.8 |
| | ⋯⋯HN⎯CH(CH(CH₃)₂)⎯CO⋯⋯ | | 164–166 (EtOH,Et₂O) | +76.3 (c = 0.46, H₂O) | 13.1 |
| | pyrrolidine-2-CO⋯⋯ | | 235–239 (EtOH,Et₂O) | −48.4 (c = 0.75, H₂O) | 21.1 |
| | ⋯⋯HN⎯C(CH₃)₂⎯CO⋯⋯ | | 285–287 (H₂O,acetone) | −67.2 (c = 1.07, DMSO) | 17.4 |
| | ⋯⋯HN⎯CH(CH₂Ph)⎯CO⋯⋯ | ⋯HN(CH₂)₅NH₃ | 228–230 dec (t-amylalcohol, Et₂O) | −29.0 (c = 0.21, H₂O) | 9.2 |
| 5-Cl-naphthalene-1-SO₂⋯⋯ | ⋯⋯HN⎯CH(CH₂Ph)⎯CO⋯⋯ | ⋯HN⎯C₆H₄⎯C₆H₅ | 190–192 (EtOAc) | +44.5 (c = 0.89, DMSO) | 51.0 |
| | ⋯⋯HN⎯C(CH₃)₂⎯CO⋯⋯ | | 186–187 (EtOAc) | −9.7 (c = 0.775, acetone) | 43.4 |
| | ⋯⋯HN⎯CH(CH(CH₃)₂)⎯CO⋯⋯ | | 218–219 (acetone, hexane) | +47.9 (c = 0.94, acetone) | 64.5 |
| | pyrrolidine-2-CO⋯⋯ | | 180–181 (EtOH) | −104.0 (c = 0.64, acetone) | 54.4 |
| | | | 192–193 (EtOH) | — | 77.3 |

TABLE 6-continued

| | | | analysis | MS, m/e [%] | ID |
|---|---|---|---|---|---|
| | ----HN—C₆H₅ | | | 135–136 (EtOH) Lit[10]: 138 (EtOH,H₂O) | — | 77.6 |
| 5-Cl-naphthyl-SO₂---- | ----HN-CH(CH₂Ph)-CO---- | ----N(piperazine)NH | $C_{23}H_{24}ClN_3O_3S \cdot HCl$ *0.5 t-amylalcohol (C,H,N) | | 21 |
| | ----HN-CH(iPr)-CO---- | | $C_{19}H_{24}ClN_3O_3S$ *0.5 EtOH*0.5 H₂O (C,H,N) | | 22 |
| | pyrrolidine-N, CO---- | | $C_{19}H_{22}ClN_3O_3S \cdot HCl$ *0.25 Et₂O (C,H,N) | | 23 |
| | ----HN-C(CH₃)₂-CO---- | | $C_{17}H_{20}ClN_3O_3S$ *0.25 acetone *0.25 H₂O (C,H,N) | | 24 |
| | ----HN-CH(CH₂Ph)-CO---- | ...HN(CH₂)₆NH₃ | $C_{25}H_{30}ClN_3O_3S \cdot HCl$ *0.5 t-amylalcohol (C,H,N) | | 25 |
| 5-Cl-naphthyl-SO₂---- | ----HN-CH(CH₂Ph)-CO---- | | $C_{31}H_{25}ClN_2O_3S$ (C,H,N) | 540 (65) | 26 |
| | ----HN-CH(CH₃)-CO---- | | $C_{25}H_{21}ClN_2O_3S$ (C,H,N) | 464 (40) | 27 |
| | ----HN-CH(iPr)-CO---- | | $C_{27}H_{25}ClN_2O_3S$ (C,H,N) | 492 (28) | 28 |
| | pyrrolidine-N, CO---- | | $C_{27}H_{23}ClN_2O_3S$ (C,H,N) | 490 (14) | 29 |
| | | | $C_{22}H_{16}ClNO_2S$ (C,H,N) | 393 (40) | 30 |
| | ----HN—C₆H₅ | | $C_{16}H_{12}ClNO_2S$ (C,H,N) | 317 (56) | 43 Lit[10] |

TABLE 7

| | | | mp, [°C.] (cryst. from) | $[\alpha]_D^{20}$, [°] | yield [%] |
|---|---|---|---|---|---|
| isoquinoline-SO₂— | —HN-CH(CH₂Ph)-CO— | piperazine-NH | 238–240 dec (EtOH, t-amyl-alcohol) | −58.2 (c = 0.3, H₂O) | 21.4 |
| | —HN-CH(iPr)-CO— | | 267–269 dec (amorphous) | +66.4 (c = 0.42, DMSO) | 13.4 |
| | prolyl (N-CO) | | 235–237 dec (EtOH, Et₂O, t-amylalcohol) | −21.3 (c = 0.23, H₂O) | 16.9 |
| | —HN-CH(CH₃)-CO— | | 240–242 dec (MeOH, Et₂O) | +36.4 (c = 1,43, H₂O) | 11.9 |
| | —HN-CH(CH₂Ph)-CO— | ...HN(CH₂)₆NH₂ | 253–255 dec (t-amylalcohol) | −112.7 (c = 0.73, H₂O) | 33.5 |
| | | —HN-biphenyl | 115–116 (acetone) | +21.8 (c = 1.13, acetone) | 24.1 |
| isoquinoline-SO₂— | —HN-CH(iPr)-CO— | —HN-biphenyl | 224–225 (acetone, pet. ether) | +95.4 (c = 0.87, acetone) | 25.7 |
| | prolyl (N-CO) | | 170–172 (EtOH) | −113.5 (c = 0.965, acetone) | 59.4 |
| | —HN-CH(CH₃)-CO— | | 185–186 (acetone, pet. ether) | +22.8 (c = 0.63, acetone) | 38.4 |
| | prolyl (N-CO) | | 178–179 (EtOH) | +113.2 (c = 1.095, aceotne) | 58.8 |
| | | | 174–175 (acetone, pentane) | — | 32.8 |
| | | —HN-phenyl | 154–155 dec (acetone, Et₂O) | — | 32.1 |

TABLE 7-continued
| | | | analysis | MS, m/e [%] | ID |
|---|---|---|---|---|---|
| 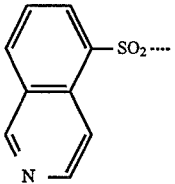 | 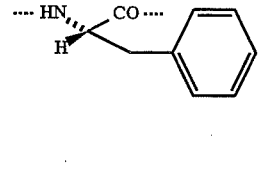 | 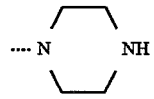 | C$_{22}$H$_{24}$N$_4$O$_3$S*2HCl *H$_2$O (C,H,N) | | 31 |
| | 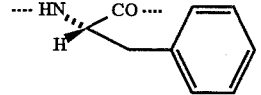 | | C$_{18}$H$_{24}$N$_4$O$_3$S*2HCl *0.5 EtOH*H$_2$O (C,H,N) | | 32 |
| | 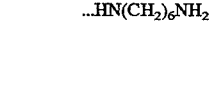 | | C$_{18}$H$_{22}$N$_4$O$_3$S*2HCl | | 33 |
| | 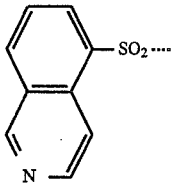 | | C$_{16}$H$_{20}$N$_4$O$_3$S*2HCl *0.5 MeOH*H$_2$O (C,H,N) | | 34 |
| | 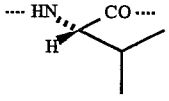 | ...HN(CH$_2$)$_6$NH$_2$ | C$_{24}$H$_{30}$N$_4$O$_3$S*2HCl *0.25 t-amylalcohol (C,H,N) | | 35 |
| | | 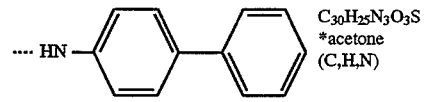 | C$_{30}$H$_{25}$N$_3$O$_3$S *acetone (C,H,N) | 507 (21) | 36 |
|  |  | 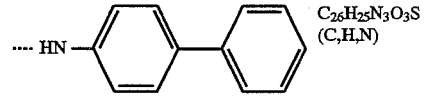 | C$_{26}$H$_{25}$N$_3$O$_3$S (C,H,N) | 459 (37) | 37 |
| | | | C$_{26}$H$_{23}$N$_3$O$_3$S (C,H,N) | 457 (35) | 38 |
| | | | C$_{24}$H$_{21}$N$_3$O$_3$S (C,H,N) | 431 (35) | 39 |
| | | | C$_{26}$H$_{23}$N$_3$O$_3$S (C,H,N) | 457 (32) | 40 |
| | | | C$_{21}$H$_{16}$N$_2$O$_2$S (C,H,N) | 360 (53) | 41 |
| | | 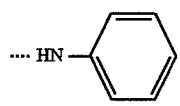 | C$_{15}$H$_{12}$N$_2$O$_2$S (C,H,N) | 284 (49) | 42 |

TABLE 8

$^1$H-NMR (300 MHz, D$_2$O)

| ID | H—C(2) H—C(6) | H—C(3) H—C(5) | H—C(4) | H—C(1') | H—C(2') | H—C(3') | H—C(5') H—C(6') H—C(7') | H$_3$C—C(1') | H$_3$C—C(2') | H—C(4')/ H—C(8') | H—C(1") H—C(2") H—C(3") H—C(4") |
|---|---|---|---|---|---|---|---|---|---|---|---|
| 1 | 7.82 m | 7.62 m | 7.73 m | 4.52 dxd (9.84, 6.10) | 3.06, 2.91 2xdx (12.97, 6.06) (12.96, 9.88) | | 7.36 m | | | 7.20 m | 1.73 (1) 2.67 (1) 2.85 (1) 2.93–3.01 (2) 3.24 (1) 3.35 (1) 3.68 (1) all m |
| 2 | 7.88 m | 7.67 m | 7.76 m | 4.43 q (6.96) | | | | 1.28 d (6.96) | | | 3.01 (1) 3.16 (1) 3.23 (1) 3.31 (1) 3.56 (2) 3.80 (2) all m |
| 3 | 7.87 br d | 7.66 m | 7.76 br 1 | 4.05 d (6.78) | 1.93 "sextex" | | | | 0.89, 0.93 2d (6.72, 6.76) | | 2.89 (1) 3.01 (1) 3.14–3.27 (2) 3.43–3.60 (2) 3.68 (1) 3.80 (1) all m |
| 4 | 7.90 m | 7.69 m | 7.79 m | 4.69 m | 1.71 (1) 1.90 (2) 2.15 (1) | | | | | | 3.30–3.42 (5) 3.55 (1) 3.81 (1) 3.89–3.07 (3) all m |

TABLE 9

$^1$H-NMR (300 MHz, D$_2$O)

| ID | H—C(2) H—C(6) | H—C(3) H—C(5) | H—C(4) | H—C(1') | H—C(4')/ H—C(8') | H—C(5') H—C(6') H—C(7') | H—C(2') | H—C(1") H—C(2") H—C(3") H—C(4") H—C(5") H—C(6") |
|---|---|---|---|---|---|---|---|---|
| 5 | 7.72 2br d | 7.54 br t | 7.67 br t | 3.94 t (7.75) | 7.11 m | 7.26 m | | 1.05 (2) 1.18–1.28 (4) 1.60 (2) 2.74 (1) 2.84–2.99 (5) all m |
| 6 | 7.72 2br d | 7.55 br t | 7.68 br t | 3.95 t (7.83) | 7.11 m | 7.27 m | 2.92 (2) d (7.98) | 1.60 br q (2) 2.60 (2) 2.91 (1) 3.02 (1) m |

TABLE 10

| | 1H-NMR (300 MHz, acetone-d6 (7) or DMSO-d6 (12)) | | | | | | | |
|---|---|---|---|---|---|---|---|---|
| ID | H—C(3) H—C(5) | H—C(4) | H—C(2") H—C(6") | H—C(10") | H—C(9") H—C(11") | H—C(3") H—C(5") | H—C(2) H—C(6) | H—C(8") H—C(12") |
| 7 | 7.48–8.58 (5) m | | | 7.33 br t | 7.44 (4) m | | 7.77 br d | 7.63 br d |
| 12 | | | 7.35–7.53 (8) m | | | 7.61 d (8.55) | | 7.68 (4) m |

| ID | H—C(1') | H—C(2') | H—C(4')/ H—C(8') | H—C(5') H—C(6') H—C(7') | NHSO2- | NHCO- |
|---|---|---|---|---|---|---|
| 7 | 4.29 br t | 2.94, 3.12 2xdx (13.70, 7.85) (13.70, 6.58) | | 7.20 (5) m | 6.97 br s | 9.29 s |
| 12 | 4.07 m | 2.71, 2.90 2dxd (13.55, 8.63) (13.61, 6.14) | 7.02 br d | 6.66 (2) d (8.29) | | 10.36 brs |

TABLE 11

| | 1H-NMR (300 MHz, acetone-d6) | | | | | | | | |
|---|---|---|---|---|---|---|---|---|---|
| ID | H—C(2) H—C(6) | H—C(3) H—C(5) | H—C(4) | H—C(8") H—C(12") | H—C(3") H—C(5") | H—C(2") H—C(6") | H—C(9") H—C(11") | H—C(10") | H—C(1') |
| 8 | 7.93 2br d | | | 7.53–7.65 (9) m | | | 7.44 br t | 7.33 br t | 4.08 q (7.06) |
| 9 | | 7.88 m | | | | 7.41–7.64 (11) m | | 7.33 br t | 3.81 m |
| 10 | 7.97 2br d | 7.82 2br d | 7.77 m | 7.70 2d | 7.66 (4) m | | 7.46 2br t | 7.34 br t | 4.27 m |

| ID | H—C(2') | H—C(3') | H—C(4')/ H—C(8') | H—C(5') H—C(6') H—C(7') | H3C—C(1') | H3C—C(2') | NHSO2- | NHCO- |
|---|---|---|---|---|---|---|---|---|
| 8 | | | | | 1.33 d (7.06) | | 6.98 br s | 9.31 s |
| 9 | 2.08 m | | | | | 0.96, 0.97 2d (6.75, 6.79) | 6.71 d (9.08) | 9.33 br s |
| 10 | 1.66, 1.81, 1.93, 2.11 (4) m | | 3.34, 3.64 2dxdxd (9.98, 7.92, 6.95 (10.0, 6.94, 4.26 | | | | | 9.41 s |

TABLE 12

| | 1H-NMR (300 MHz, DMSO-d6) | | | | | | | |
|---|---|---|---|---|---|---|---|---|
| ID | H—C(2) H—C(6) | H—C(8") H—C(12") | H—C(3) H—C(5) | H—C(4''') | H—C(7''') | H—C(4) | H—C(9") H—C(11") | H—C(10") |
| 11 | 7.68, 7.72 (4) 2br d | | | 7.49 (4) m | | | 7.38 (4) br t | |

| ID | H—C(1') | H—C(2') | H—C(2''') | H—C(5''') | H—C(6''') | H—C(3") H—C(5") | H—C(2") H—C(6") | NH- |
|---|---|---|---|---|---|---|---|---|
| 11 | 4.26 | 3.12, 3.29 | 7.16 | 6.98 | 7.10 | | 7.58 (4) | 10.97 |

TABLE 12-continued

$^1$H-NMR (300 MHz, DMSO-$d_6$)

| br t | 2dxd<br>(14.45, 7.02)<br>(14.45, 6.8) | br s | dxd<br>(7.55, 7.19) | t<br>(7.48) | m | br s |
|---|---|---|---|---|---|---|

TABLE 13

$^1$H-NMR (300 MHz, D$_2$O)

| ID | H—C(2)<br>H—C(6) | H—C(3)<br>H—C(5) | H—C(1') | H$_3$C—C(1') | H$_3$C—C(2') | H—C(3') | H—C(2') | H—C(1")<br>H—C(2")<br>H—C(3")<br>H—C(4") | H—C(4')/<br>H—C(8') | H—C(5')<br>H—C(6')<br>H—C(7') |
|---|---|---|---|---|---|---|---|---|---|---|
| 13 | 7.82<br>m | 7.20<br>m | 4.53<br>dxd<br>(9.38, 6.47) | | | | | 1.84 (1)<br>2.65 (1)<br>2.89–3.12 (5)<br>3.37 (1)<br>3.47 br d (1)<br>3.78 br d (1)<br>all m | | 7.33 (5)<br>m |
| 14 | 7.92<br>2 br d | 7.38<br>m | 4.45<br>q<br>(6.95) | 1.28<br>d<br>(6.95) | | | | 3.12 (1)<br>3.22–3.37 (3)<br>3.63–3.68 (2)<br>3.80–3.90 (2)<br>all m | | |
| 15 | 7.91, 7.92<br>2br d | 7.38<br>br t | 4.07<br>d<br>(6.75) | | 0.87, 0.93<br>2d<br>(6.70, 6.75) | | 1.94<br>"sextet" | 3.03 (1)<br>3.12–3.31 (3)<br>3.50 (1)<br>3.63–3.78 (2)<br>3.88 (1)<br>all m | | |
| 16 | 7.94<br>2br d | 7.40<br>br t | 4.71<br>m | | | 1.73 (1)<br>1.92 (2)<br>2.19 (1)<br>m | | 3.33—3.44 (5)<br>3.54 (1)<br>3.81–3.87 (1)<br>3.91–4.07 (3)<br>all m | | |

TABLE 14

$^1$H-NMR (300 MHz, acetone-$d_6$)

| ID | H—C(2)<br>H—C(6) | H—C(3)<br>H—C(5) | H—C(1') | H—C(2') | H—C(3') | H—C(4')/<br>H—C(8') | H—C(5')<br>H—C(6')<br>H—C(7') | H$_3$C—C(1') |
|---|---|---|---|---|---|---|---|---|
| 17 | 7.79<br>2br d | 7.11<br>m | 4.26<br>dxd<br>(8.45, 6.25) | 2.96, 3.41<br>2dxd<br>(13.73, 8.45)<br>(13.73, 6.19) | | 7.19 (5)<br>m | | |
| 18 | 7.97<br>2br d | 7.30<br>br d | 4.10<br>q<br>(7.06) | | | | | 1.35<br>d<br>(7.06) |
| 19 | 7.95, 7.93<br>2br d<br>(9.06)<br>(9.04) | 7.23, 7.20<br>2br d | 3.80<br>m | 2.08<br>m | | | | |
| 20 | 8.05<br>2br d | 7.81<br>br d | 4.28<br>m | 1.71, 1.84–2.00, 2.13 (4)<br>m | | 3.63, 3.35<br>2dxdxd<br>(9.99, 6.94, 4.64<br>(9.87, 7.91, 6.76 | | |

| ID | H$_3$C—C(2') | H—C(8")<br>H—C(12") | H—C(3")<br>H—C(5") | H—C(2")<br>H—C(6") | H—C(9")<br>H—C(11") | H—C(10") | NHSO$_2$- | NHCO- |
|---|---|---|---|---|---|---|---|---|
| 17 | | 7.61<br>br d | 7.55 (4)<br>br s | 7.43<br>br t | 7.32<br>br t | | | 9.29<br>s |

TABLE 14-continued

| | | ¹H-NMR (300 MHz, acetone-d₆) | | | | | |
|---|---|---|---|---|---|---|---|
| 18 | | 7.58–7.65 (6) m | | 7.45 br t | 7.33 br t | 7.06 br s | 9.34 s |
| 19 | 0.97 (d) d (6.84) | 7.63 m | 7.56 (4) m | 7.45 2br t | 7.33 br t | 6.83 m | 9.42 br s |
| 20 | | 7.65 (4) m | | 7.45 (4) m | | 7.34 br t | 9.41 s |

TABLE 15

| | ¹H-NMR (300 MHz, DMSO-d₆ (21), D₂O) | | | | | | | |
|---|---|---|---|---|---|---|---|---|
| ID | H—C(2) | H—C(3) | H—C(7) | H—C(8) | H—C(4) | NHSO₂- | H—C(6) | H—C(1') |
| 21 | 8.63 d (8.83) | 8.04 dxd (9.19, 7.72) | 7.73, 7.58* 2dxd (8.09, 7.73) | 8.46, 8.19* 2d (8.09, 8.46) | 7.69 m | | 8.12, 7.86* 2d (7.36, 7.35) | 4.37 t (7.36) |
| 22 | 8.56 d (8.46) | 7.65 dxd (8.09, 7.72) | 7.80 br dxd (8.09, 7.36) | 8.25 d (7.36) | 7.72 d (7.35) | 7.68 br s | 8.08 d (7.72) | 3.91 d (7.35) |
| 23 | 8.63 d (8.49) | 7.65–7.80 m | | 8.26 m | | | 8.09 d (8.08) | 5.00 m |
| 24 | 8.58 br d (8.24) | 7.66 dxd (7.88, 7.77) | 7.72 dxd (7.50) | 8.26 br d (7.45) | 7.80 dxd (7.74, 1.42) | 8.24 s | 8.09 br d (7.98) | 4.37 q (6.96) |

| ID | H—C(3') | H—C(2') | H—C(1")<br>H—C(2")<br>H—C(3")<br>H—C(4") | H—C(4')/<br>H—C(8') | H—C(5')<br>H—C(6')<br>H—C(7') | H₃C—C(1') | H₃—C(2') |
|---|---|---|---|---|---|---|---|
| 21 | | | 2.00 (1)<br>2.36 (2)<br>2.66–2.83 (3)<br>3.03 (2)<br>3.19–3.33 (2)<br>all m | 7.13 (2) m | 7.06 m | | |
| 22 | | 1.86 "sextet" | 2.63 (1)<br>2.81 (1)<br>3.05 (3)<br>3.25–3.42 (2)<br>3.64 (1)<br>all m | | | | 0.82, 0.85 2d |
| 23 | 1.85–2.05 (3)<br>2.27 (1)<br>m | | 3.13 (1)<br>3.26 (3)<br>3.54–3.91 (6)<br>all m | | | | |
| 24 | | | 2.73 (1)<br>2.89 (1)<br>3.05–3.27 (4)<br>3.51–3.62 (2)<br>all m | | | 1.21 d (6.98) | |

*doubling of the signals

TABLE 16

| | ¹H-NMR (300 MHz, D₂O) | | | | | | |
|---|---|---|---|---|---|---|---|
| ID | H—C(1) | H—C(2) | H—C(7) | H—C(3) | H—C(4) | H—C(6) | H—C(8) |
| 25 | | 8.63 d (8.38) | 7.65–7.80 m | | 7.90 m | 8.09 d (7.82) | 8.25 d (7.39) |
| 35 | 9.66 s | | 8.02 dxd (8.09, 7.72) | 8.52 m | | 8.61 2d (7.72) | |

| | H—C(4')<br>H—C(5')<br>H—C(6')<br>H—C(7') | | | H—C(1") | H—C(2")<br>H—C(3")<br>H—C(4") | | |

TABLE 16-continued $^1$H-NMR (300 MHz, D$_2$O)

| ID | H—C(1') | H—C(8') | H—C(2') | H—C(6") | H—C(5") | NH.. |
|---|---|---|---|---|---|---|
| 25 | 3.88 "t" (7.38) | 6.87 (5) m | 3.02–3.13 (6) m | | 1.45 (6) 1.77 (2) m | |
| 35 | 3.88 dxd (11.40, 4.41) | 6.68 (5) m | 2.96, 2.62 2dxd (14.52, 4.23) (14.13, 11.21) | 3.16, 3.02 (4) m | 1.32–1.55 (6) 1.69 (2) m | 8.36 br t |

TABLE 17

$^1$H-NMR (300 MHz, acetone-d$_6$, CDCl$_3$ (43))

| ID | H—C(2) | H—C(3) | H—C(4) | H—C(6) | H—C(8) | H—C(7) | H—C(1') | H—C(2') | H—C(3') | H—C(4')/ H—C(8') |
|---|---|---|---|---|---|---|---|---|---|---|
| 26 | 8.67 br d (8.72) | 7.62 dxd (8.69, 7.52) | 7.75 dxd (7.52, 0.94) | 8.21 dxd (7.36, 1.18) | 8.37 br d (8.55) | 7.60 dxd (8.57, 7.35) | 4.24 dxd (9.02, 5.73) | 2.85, 3.07 2dxd (13.80, 9.02) (13.80, 5.73) | | 7.01 m |
| 27 | 8.84 br d (8.67) | 7.70 dxd (8.64, 7.57) | 7.80 br d (7.51) | 8.38 dxd (7.35, 1.14) | 8.46 br d (8.56) | 7.73 dxd (8.53, 7.39) | 4.10 q (7.06) | | | |
| 28 | 8.85 d (8.60) | 7.68 dxd (8.44, 7.54) | 7.76 dxd (7.48, 1.06) | 8.36 2br d | | 7.67 dxd (8.53, 7.26) | 3.72 d (7.32) | 2.00 m | | |
| 29 | 8.97 br d (8.72) | 7.71 dxd (8.72, 7.56) | 7.82 dxd (7.50, 0.96) | 8.44 dxd (7.40, 1.12) | 8.58 br d (8.55) | 7.82 dxd (8.54, 7.43) | 4.50 m | 1.84, 2.06, 2.14 m | | 3.63 m |
| 30 | 8.86 d (8.70) | 7.71 dxd (8.52, 7.71) | 7.82 d (7.40) | 8.42 br d (7.35) | 8.56 d (8.57) | 7.78 dxde (8.36, 7.35) | | | | |
| 43 | 8.67 br d (8.82) | 7.56 dxd (8.82, 7.36) | 7.69 dxd (7.35, 1.10) | 8.27 dxd (7.35, 1.10) | 8.54 br d (8.46) | 7.57 dxd (8.45, 7.35) | | | | |

| ID | H—C(6') H—C(7') | H$_3$C—C(1') | H$_3$C—C(2') | H—C(3") H—C(5") | H—C(2") H—C(6") | H—C(9") H—C(11") | H—C(8") H—C(12") | H—C(10") | NHCO.. | NHSO$_2$.. |
|---|---|---|---|---|---|---|---|---|---|---|
| 26 | 6.92 m | | | | 7.44–7.54 m | | 7.64 br d | 7.34 br t | 9.22 s | |
| 27 | | 1.28 d (7.06) | | 7.37 m | 7.51 br d | 7.44 br t | 7.62 2d | 7.33 br t | 9.09 s | |
| 28 | | | 0.84, 0.92 2d (6.72) | 7.24 m | | 7.46 m | 7.61 2d | 7.33 br t | 9.07 br s | 7.15 br s |
| 29 | | | | | 7.56 m | 7.45 br t | 7.64 2d | 7.33 br t | 9.13 s | |
| 30 | | | | 7.47 br d (8.60) | 7.22 br d (8.61) | 7.39 br t | 7.52 br d | 7.29 br t (7.27) | | 9.61 s |
| 43 | | | | | | 7.04–7.14 m | | 6.93 m [H—C(4")] | | 6.93 m |

TABLE 18

$^1$H-NMR (300 MHz, D$_2$O)

| ID | H—C(1) | H—C(3) | H—C(4) | H—C(8) | H—C(6) | H—C(7) | H—C(1') |
|---|---|---|---|---|---|---|---|
| 31 | 9.72 s | | 8.59 s | | 8.65 2br d | 8.05 "t" | 4.43 dxd (10.30, 5.89) |
| 32 | 9.85 s | 9.06 d (6.99) | 8.78 d (6.99) | 8.77 d (7.73) 8.82 dxd (8.45, 1.10) | | 8.16 "t" (8.09) | 4.11 d (6.98) |

TABLE 18-continued

¹H-NMR (300 MHz, D₂O)

| 33 | 9.83 s | 9.10 d (6.91) | 8.75 m | | 8.81 d (7.47) | 8.16 "t" (7.94) | 5.01 m |
|----|--------|---------------|--------|--|---------------|-----------------|--------|
| 34 | 9.71 s | 8.85 d (6.77) | 8.71 d (6.77) | 8.65 d (8.31) | 8.69 d (7.50) | 8.05 "t" (7.90) | 4.51 q (7.03) |

| ID | H—C(2') | H—C(3') | H—C(5')<br>H—C(6')<br>H—C(7') | H—C(4')/<br>H—C(8') | H—C(1")<br>H—C(2")<br>H—C(3")<br>H—C(4") | H₃C—C(1') | H₃C—C(2') |
|----|---------|---------|-------------------------------|---------------------|-------------------------------------------|-----------|-----------|
| 31 | 2.74, 2.90<br>2dxd<br>(13.78, 10.48)<br>(13.79, 5.70) | | 6.82 (5)<br>m | | 2.89 (1)<br>3.13–3.33 (3)<br>3.62–3.85 (4)<br>all m | | |
| 32 | 1.90<br>"sextet" | | | | 3.03 (1)<br>3.17 (1)<br>3.23 (2)<br>3.36 (1)<br>3.57 (1)<br>3.76 (1)<br>3.89 (1)<br>all m | | 0.72, 0.81<br>2d<br>(6.62) |
| 33 | | 1.98 (3)<br>2.36 (1)<br>m | | | 3.36 (4)<br>3.55 (2)<br>3.73–3.90 (2)<br>3.91–4.05 (2)<br>all m | | |
| 34 | | | | | 3.02 (1)<br>3.30 (5)<br>3.78 (2)<br>all m | 1.21<br>d<br>(7.03) | |

TABLE 19

¹H-NMR (300 MHz, acetone-d₆)

| ID | H—C(1) | H—C(3) | H—C(4) | H—C(6) | H—C(8) | H—C(7) | H—C(1') | H—C(2') | H—C(3') | H—C(4')/<br>H—C(8') |
|----|--------|--------|--------|--------|--------|--------|---------|---------|---------|---------------------|
| 36 | 9.27 s | 8.57 d (6.07) | 8.37 d (6.10) | 8.13, 8.17 2d (7.37, 8.27) | | in the region 7.53–7.64 m | 4.08 dxd (9.53, 4.89) | 2.75, 2.90 2dxd (13.60, 9.75) (13.60, 4.80) | | 7.02 m |
| 37 | 9.31 br s | 8.69 d (6.14) | 8.61 br d (6.07) | 8.45 dxd (7.36, 1.35) | 8.22 br d (8.26) | 7.69 dxd (8.15, 7.45) | 3.78 m | 2.03 m | | |
| 38 | 9.43 br s | 8.72 br d | 8.69 d (6.16) | 8.55 dxd (7.39, 1.24) | 8.43 br d (8.21) | 7.85 dxd (8.15, 7.47) | 4.55 m | 1.81, 2.05–2.13, m | | 3.57, 3.68 m |
| 39 | 9.39 br s | 8.70 br d | 8.60 br d | 8.47 d (7.34) | 8.31 d (8.18) | 7.74 br t | 4.14 m | | | |
| 41 | 9.43 br s | 8.69 d (6.08) | 8.58 d (6.15) | 8.51 dxd (7.39, 1.05) | 8.39 d (8.22) | 7.79 t (7.83) | | | | |
| 42 | 9.42 d (0.66) | 8.67 d (6.10) | 8.54 br d (6.07) | 8.45 dxd (7.39, 1.17) | 8.39 d (8.22) | 7.78 br t (7.82) | | | | |

| ID | H—C(5')<br>H—C(6')<br>H—C(7') | H₃C—C(1') | H₃C—C(2') | H—C(3")<br>H—C(5") | H—C(2")<br>H—C(6") | H—C(9")<br>H—C(11") | H—C(8")<br>H—C(12") | H—C(10") | NHCO- | NHSO₂- |
|----|-------------------------------|-----------|-----------|--------------------|--------------------|---------------------|---------------------|----------|-------|--------|
| 36 | 6.89 m | | | | 7.38–7.47, 7.53–7.64 m | | | | 7.33 br t | 10.23 s |
| 37 | | | 0.86, 0.91 2d (6.72) | 7.41–7.50 m | | 7.27–7.35, 7.61 m | | | 9.20 br s | |
| 38 | | | | 7.58–7.66 m | 7.44 br t | 7.58–7.66 m | | 7.33 br t | 9.42 s | |
| 39 | | 1.30 d | | 7.39–7.51 m | 7.43 m | 7.61 br d | 7.33 br t | 9.23 br s | 7.55 br s |

TABLE 19-continued

| | ¹H-NMR (300 MHz, acetone-d₆) | | | | | | |
|---|---|---|---|---|---|---|---|
| 41 | (7.05) | 7.48 br d (8.64) | 7.23 br d (8.66) | 7.39 br t | 7.52 br d (7.32) | 7.29 br t | 9.66 br s |
| 42 | | | 7.15 m | | | 7.00 br t [H—C(4")] | 9.51 br s |

TABLE 20

| ID | IC₅₀[1] (μM) |
|---|---|
| 1 | promotion[2] |
| 2 | promotion[3] |
| 7 | 310 |
| 10 | 520 |
| 11 | 570 |
| 21 | 600 |
| 22 | 310 |
| 25 | 67 |
| 30 | 275 |
| 31 | promotion[4] |
| 35 | 263 |
| 37 | 470 |
| 38 | 130 |
| 40 | 435 |
| 41 | promotion[5] |
| 43 | 190 |

[1] Compounds are only listed if their IC₅₀ is lower than 600 μM.
[2] Promotion of the hydrolysis rate at 100 mM: 138% of the value in absence of an inhibitor.
[3] Promotion of the hydrolysis rate at 100 mM: 125% of the value in absence of an inhibitor.
[4] Inhibition at 100 μM: 70.1%, at 300 μM 54.0%.
[5] Inhibition at 10 μM: 31.6%, at 100 μM 28.3%.

I claim:

1. Compounds of the general formula

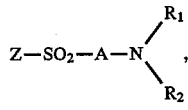

wherein

Z is phenyl, naphthyl, (5)-, or (8)-isoquinolyl, possibly substituted by halogen; except that Z is not phenyl when both A is L-proline and R₂ is phenyl;

A is selected from the group consisting of L-phenylalanine, L-alanine, L-proline, L-valine, L-tryptophane and L-tyrosine moieties, where the N atom of the α-amino group which defines A as an amino acid is bound to SO₂ and its carboxyl group to the N atom of formula I, R₁ is hydrogen, and R₂ is phenyl, biphenyl, a C₂ to C₆-alkylamine; except that R₂ is not phenyl when A is L-valine or L-alanine; or R₁ and R₂ together form the piperazine ring, except that R₁ and R₂ together do not form the piperazine ring when A is L-phenylalanine or L-tyrosine, or its pharmaceutically acceptable non-toxic acid addition salts with inorganic or organic acids.

2. Compounds of one of the formulas:

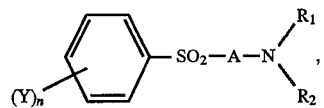

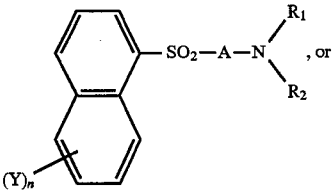

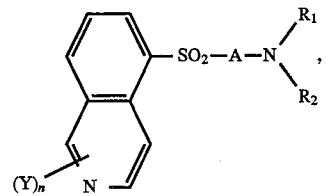

wherein

A is selected from the group consisting of L-phenylalanine, L-alanine, L-proline, L-valine, L-tryptophane and L-tyrosine moieties, where the N atom of the α-amino group which defines A as an amino acid is bound to SO₂ and its carboxyl group to the N atom of formula II, III or IV, R₁ is hydrogen, and R₂ is phenyl, biphenyl, a C₂ to C₆-alkylamine; except that R₂ is not phenyl when A is L-valine or L-alanine; or R₁ and R₂ together form the piperazine ring, except that R₁ and R₂ together do not form the piperazine ring when A is L-phenylalanine or L-tyrosine, Y is F, Cl, Br, being the same or different, and n is 0, 1 or 2;

except that compound (II) cannot have both A as L-proline and R₂ as phenyl;

or their pharmaceutically acceptable non-toxic acid addition salts with inorganic or organic acids.

3. The compounds of claim 1, wherein A is the L-phenylalanine, L-alanine, L-valine or L-proline group.

4. The compounds of claim 1, wherein A is the L-phenylalanine group.

5. Compounds of claim 1, wherein R₁ and R₂ together form the piperazine ring.

6. Compounds of claim 2 of formula III, wherein

Y is F or Cl in 5-position n is 1

R₁ is hydrogen, and

R₂ is biphenyl.

7. Compounds of claim 2 of formula IV, wherein
Y is hydrogen
n is 0
$R_1$ is hydrogen, and
$R_2$ is biphenyl.

8. A method of inhibiting $Ca^{2+}$-dependent enzymes and proteins consisting of Phospholipase $A_2$ ($PLA_2$), for the treatment of inflammation, comprising contacting the ($PLA_2$) with an effective amount of the compounds of claim 1.

9. A pharmaceutical composition for inhibiting $Ca^{2+}$-dependent enzymes and proteins, the composition comprising compounds of the formula:

$$Z-SO_2-A-N\begin{matrix}R_1\\ \\R_2\end{matrix}, \quad I$$

wherein
Z is phenyl, naphthyl, (5)- or (8)-isoquinolyl, possibly substituted by halogen; except that Z is not phenyl when both A is L-proline and $R_2$ is phenyl;

A is selected from the group consisting of L-phenylalanine, L-alanine, L-proline, L-valine, L-tryptophane and L-tyrosine moieties, where the N atom of the amino group which defines A as an α-amino add is bound to $SO_2$ and its carboxyl group to the N atom of formula I $R_1$ is hydrogen, and $R_2$ is phenyl biphenyl, a $C_2$ to $C_6$-alkylamine; except that $R_2$ is not phenyl when A is L-valine or L-alanine; or $R_1$ and $R_2$ together form the piperazine ring, except that $R_1$ and $R_2$ together do not form the piperazine ring when A is L-phenylalanine or L-tyrosine, or their pharmaceutically acceptable non-toxic acid addition salts selected from the group consisting of the salts of inorganic acids in turn selected from the group consisting of hydrochloric acid, phosphoric acid and sulfuric add; and the salts of organic acids in turn selected from the group consisting of citric acid, tartaric acid and methanesulfonic add.

10. Compounds of claim 2 wherein A is the L-phenylalanine, L-alanine, L-proline or L-valine group.

11. Compounds of claim 2 wherein A is the L-phenylalanine group.

12. Compounds of claim 2 wherein
$R_1$ is hydrogen,
$R_2$ is biphenyl.

13. Compounds of claim 3 wherein
$R_1$ is hydrogen,
$R_2$ is biphenyl.

14. Compounds of claim 4 wherein
$R_1$ is hydrogen,
$R_2$ is biphenyl.

15. Compounds of claim 2, wherein $R_1$ and $R_2$ together form the piperazine ring.

16. Compounds of claim 3, wherein $R_1$ and $R_2$ together form the piperazine ring, except that $R_1$ and $R_2$ together do not form the piperazine ring when A is L-phenylalanine.

17. Compounds of claim 15 with formula III, wherein
Y is F or Cl in 5-position
n is 1
$R_1$ is hydrogen, and
$R_2$ is biphenyl.

18. Compounds of claim 16 with formula III, wherein
Y is F or Cl in 5-position
n is 1
$R_1$ is hydrogen, and
$R_2$ is biphenyl.

19. Compounds of claim 15 with formula IV, wherein
Y is hydrogen
n is 0
$R_1$ is hydrogen, and
$R_2$ is biphenyl.

20. Compounds of claim 16 with formula IV, wherein
Y is hydrogen
n is 0
$R_1$ is hydrogen, and
$R_2$ is biphenyl.

21. A method of inhibiting $Ca^{2+}$-dependent enzymes and proteins consisting of Phospholipase $A_2$ ($PLA_2$), for the treatment of inflammation, comprising contacting the ($PLA_2$) with an effective amount of a compound of claim 2.

22. A method of inhibiting $Ca^{2+}$-dependent enzymes and proteins consisting of Phospholipase $A_2$ ($PLA_2$), for the treatment of inflammation, comprising contacting the ($PLA_2$) with an effective amount of a compound of claim 3.

23. A method of inhibiting $Ca^{2+}$-dependent enzymes and proteins consisting of Phospholipase $A_2$ ($PLA_2$), for the treatment of inflammation, comprising contacting the ($PLA_2$) with an effective amount of a compound of claim 4.

24. A method of inhibiting $Ca^{2+}$-dependent enzymes and proteins consisting of Phospholipase $A_2$ ($PLA_2$), for the treatment of inflammation, comprising contacting the ($PLA_2$) an effective amount of a compound of claim 6.

25. A method of inhibiting $Ca^{2+}$-dependent enzymes and proteins consisting of Phospholipase $A_2$ ($PLA_2$), for the treatment of inflammation, comprising contacting the ($PLA_2$) with an effective amount of a compound of claim 5.

26. A method of inhibiting $Ca^{2+}$-dependent enzymes and proteins consisting of Phospholipase $A_2$ ($PLA_2$), for the treatment of inflammation, comprising contacting the ($PLA_2$) with an effective amount of a compound of claim 6.

27. A method of inhibiting $Ca^{2+}$-dependent enzymes and proteins consisting of Phospholipase $A_2$ ($PLA_2$), for the treatment of inflammation, comprising contacting the ($PLA_2$) with an effective amount of a compound of claim 7.

28. The method of inhibiting $Ca^{2+}$-dependent enzymes and proteins consisting of Phospholipase $A_2$ ($PLA_2$), for the treatment of inflammation, comprising contacting the ($PLA_2$) an effective amount of a composition of claim 13.

29. Compounds of the general formula $$Z-SO_2-A-N\begin{matrix}R_1\\ \\R_2\end{matrix}, \quad I$$

wherein
Z is phenyl, naphthyl, (5)- or (8)-isoquinolyl, possibly substituted by halogen;

A is selected from the group consisting of L-phenylalanine, L-alanine, L-proline, L-valine, L-tryptophane and L-tyrosine moieties, where the N atom of the α-amino group which defines A as an amino acid is bound to $SO_2$ and its carboxyl group to the N atom of formula I, $R_1$ is hydrogen, and $R_2$ is biphenyl, or its pharmaceutically acceptable non-toxic acid addition salts with inorganic or organic acids.

30. Compounds of one of the formulas:

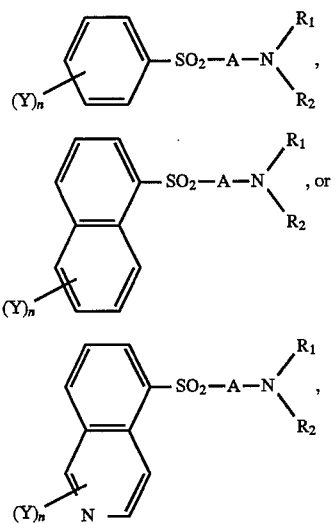

wherein
A is selected from the group consisting of L-phenylalanine, L-alanine, L-proline, L-valine, L-tryptophane and L-tyrosine moieties, where the N atom of the α-amino group which defines A as an amino acid is bound to $SO_2$ and its carboxyl group to the N atom of formula II, III or IV,
$R_1$ is hydrogen, and
$R_2$ is biphenyl,
Y is F, Cl, Br, being the same or different, and
n is 0, 1 or 2, or their pharmaceutically acceptable non-toxic acid addition salts with inorganic or organic acids.

31. A pharmaceutical composition for inhibiting $Ca^{2+}$-dependent enzymes and proteins, the composition comprising compounds of the formula:

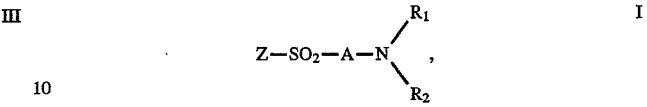

wherein

Z is phenyl, naphthyl, (5)- or (8)-isoquinolyl, possibly substituted by halogen;

A is selected from the group consisting of L-phenylalanine, L-alanine, L-proline, L-valine, L-tryptophane and L-tyrosine moieties, where the N atom of the amino group which defines A as an α-amino acid is bound to $SO_2$ and its carboxyl group to the N atom of formula I $R_1$ is hydrogen, and $R_2$ is biphenyl, or their pharmaceutically acceptable non-toxic acid addition salts selected from the group consisting of the salts of inorganic acids in turn selected from the group consisting of hydrochloric acid, phosphoric acid and sulfuric acid; and the salts of organic acids in turn selected from the group consisting of citric acid, tartaric acid and methanesulfonic acid.

* * * * *